(12) United States Patent
Griffin

(10) Patent No.: US 9,802,481 B2
(45) Date of Patent: Oct. 31, 2017

(54) VEHICLE DRIVER MONITORING SYSTEM

(71) Applicant: Brian Griffin, Wilton, CT (US)

(72) Inventor: Brian Griffin, Wilton, CT (US)

( * ) Notice: Subject to any disclaimer, the term of this patent is extended or adjusted under 35 U.S.C. 154(b) by 0 days.

(21) Appl. No.: 15/248,389

(22) Filed: Aug. 26, 2016

(65) Prior Publication Data

US 2017/0057353 A1    Mar. 2, 2017

Related U.S. Application Data

(60) Provisional application No. 62/293,195, filed on Feb. 9, 2016, provisional application No. 62/350,289, filed on Jun. 15, 2016, provisional application No. 62/211,325, filed on Aug. 28, 2015.

(51) Int. Cl.
  *B60K 28/06* (2006.01)
  *A61B 5/18* (2006.01)
  *A61B 5/00* (2006.01)

(52) U.S. Cl.
  CPC .............. *B60K 28/063* (2013.01); *A61B 5/18* (2013.01); *A61B 5/4845* (2013.01)

(58) Field of Classification Search
  CPC ........ B60K 28/063; A61B 5/4845; A61B 5/18
  USPC .......................................................... 701/45
  See application file for complete search history.

(56) References Cited

U.S. PATENT DOCUMENTS

| | | | |
|---|---|---|---|
| 6,819,248 B2 | 11/2004 | Gotfried | |
| 8,196,694 B2 * | 6/2012 | Biondo | B60K 28/063 180/271 |
| 8,466,796 B1 * | 6/2013 | Mejia | G01N 33/4972 340/573.1 |
| 8,941,501 B1 * | 1/2015 | Debijl | A45C 11/321 340/522 |
| 2004/0083031 A1 * | 4/2004 | Okezie | A61B 5/145 701/1 |
| 2008/0196963 A1 * | 8/2008 | Karlsson | B60K 28/063 180/272 |
| 2008/0250829 A1 * | 10/2008 | Kamiki | B60K 28/063 70/344 |
| 2010/0108425 A1 * | 5/2010 | Crespo | A61B 5/082 180/272 |
| 2010/0314190 A1 * | 12/2010 | Zimmermann | B60K 28/063 180/272 |
| 2011/0304465 A1 * | 12/2011 | Boult | B60K 28/06 340/576 |

* cited by examiner

*Primary Examiner* — Brian P Sweeney
(74) *Attorney, Agent, or Firm* — Chad Peterson

(57) ABSTRACT

A vehicle driver monitoring system includes a supervisor computerized device and an operator computerized device. The system may also include a key container device. The devices of the vehicle driver monitoring system work in conjunction with each other to monitor various aspects of the user's operation of a corresponding vehicle during use. If a key container device is used, the devices also work to limit the operability of a vehicle key. For example, the supervisor computerized device is configured to remotely receive vehicle monitoring information, such as location information, speed information, and operator information, from the operator computerized device as the operator drives the vehicle. Further, the optional key container device is configured to selectively allow to the operability of a vehicle key based upon vehicle access info, identity and sobriety information as related to the user and as provided by the operator computerized device.

22 Claims, 21 Drawing Sheets

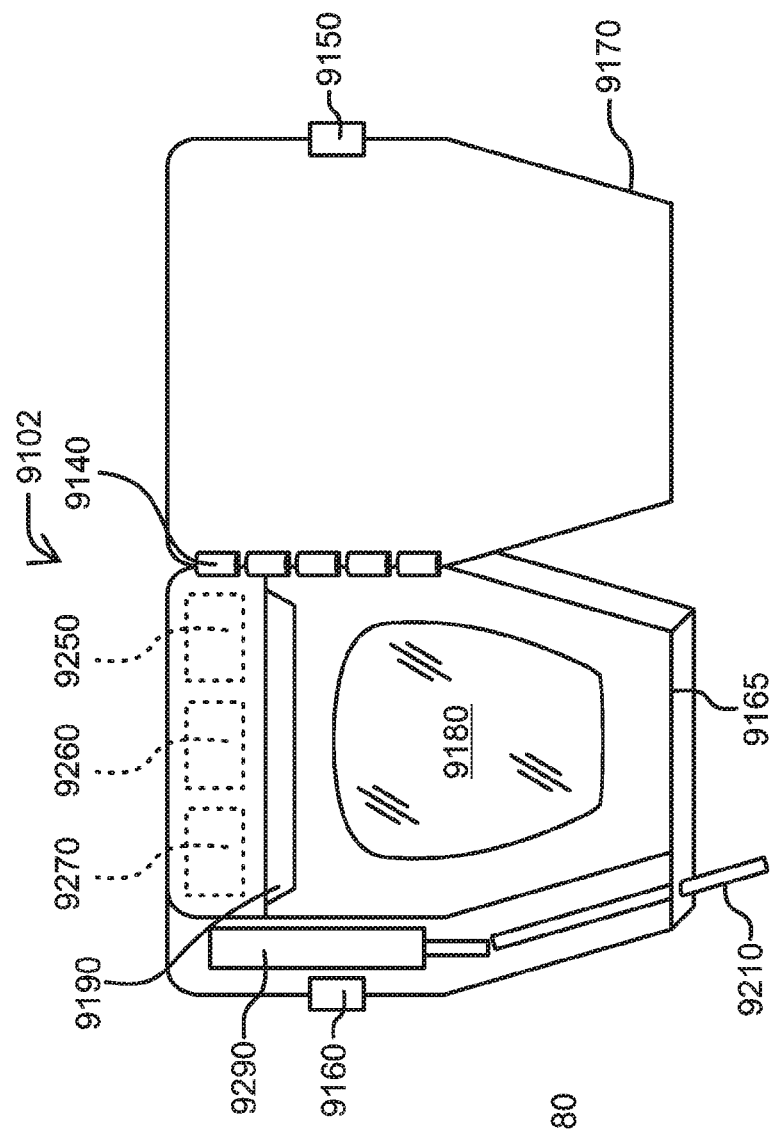
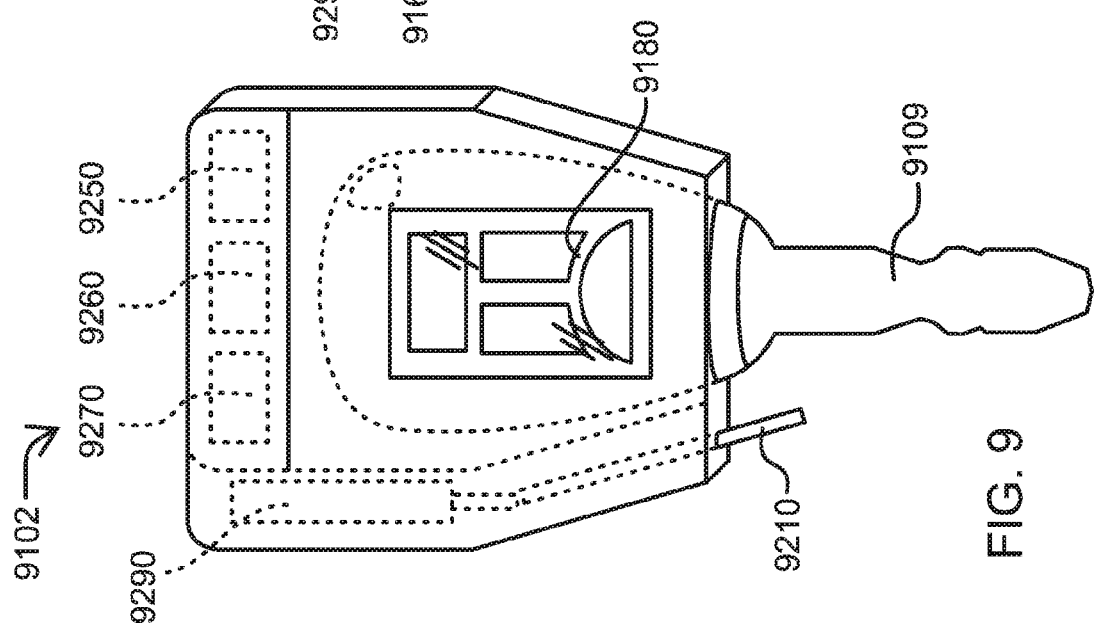

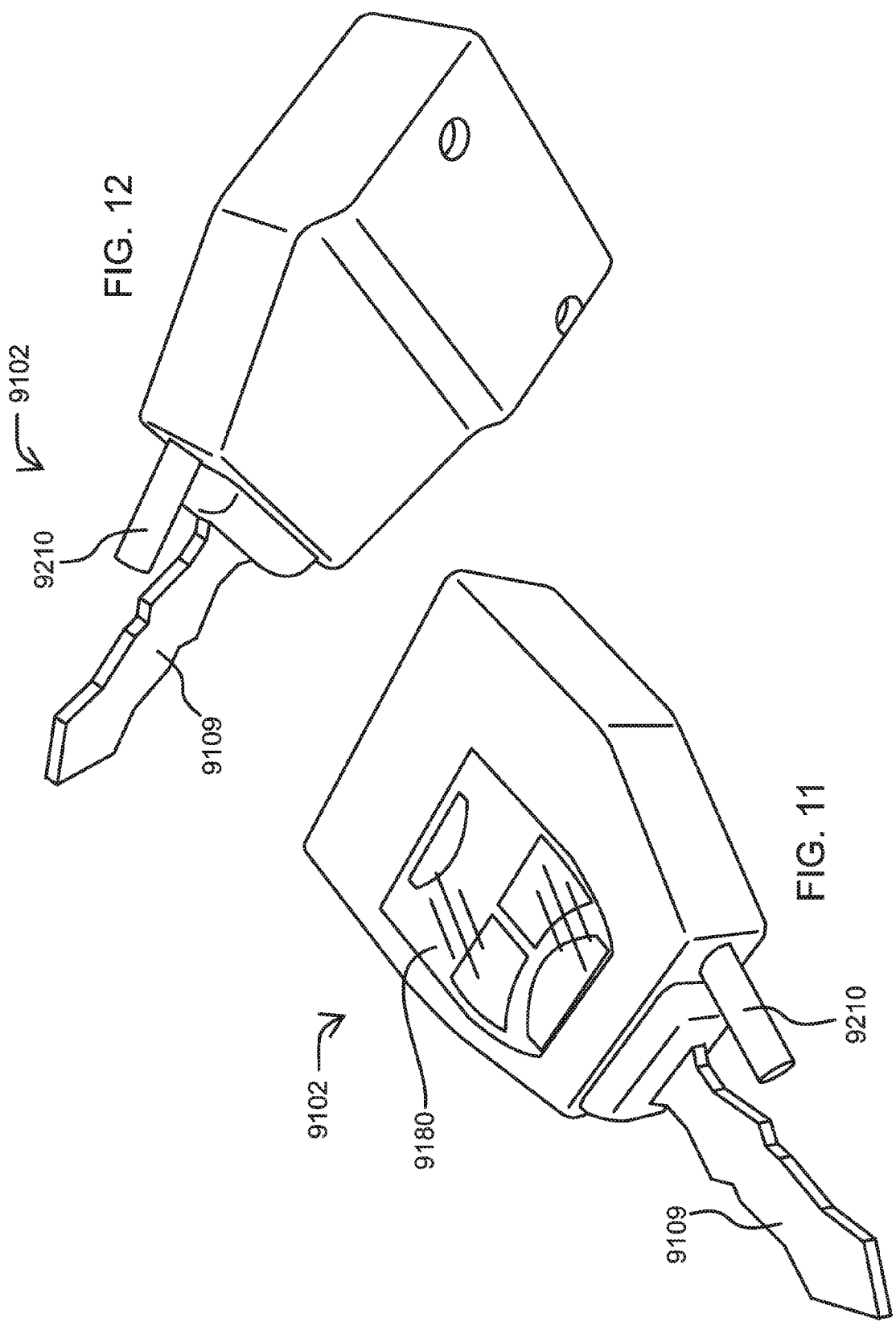

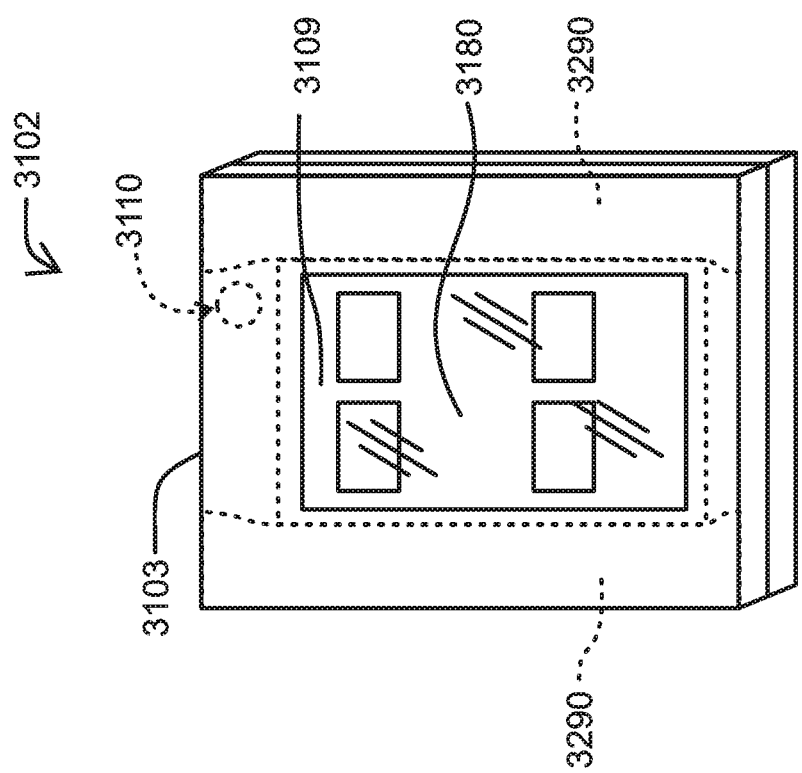

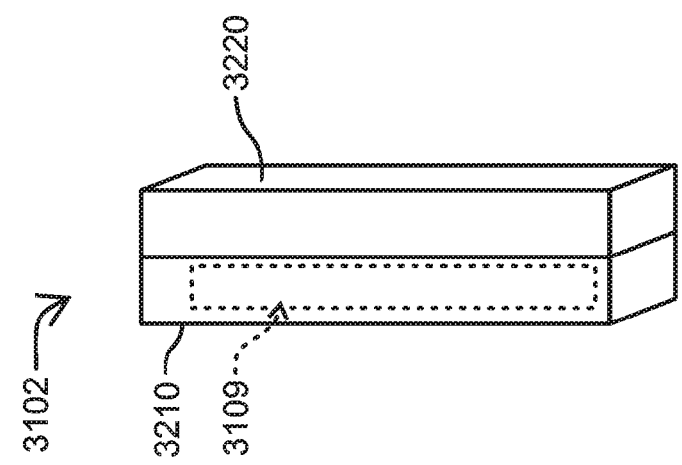
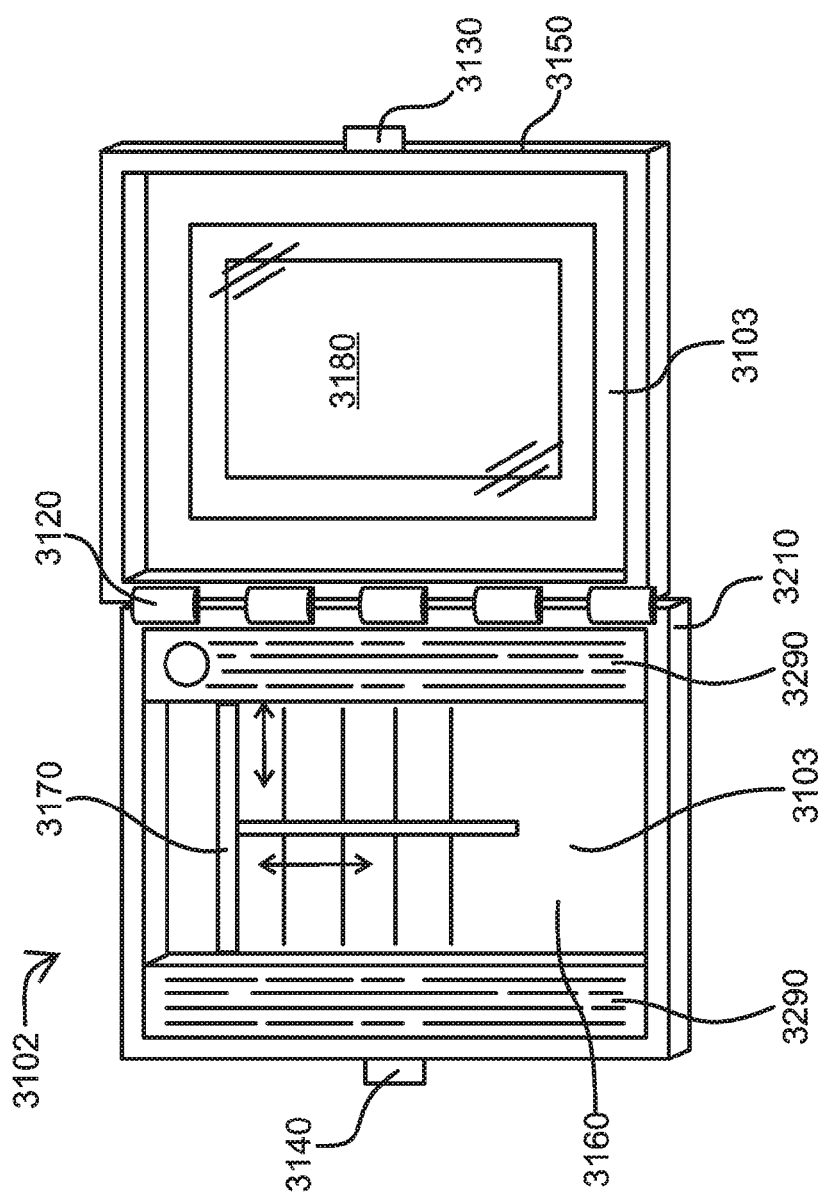

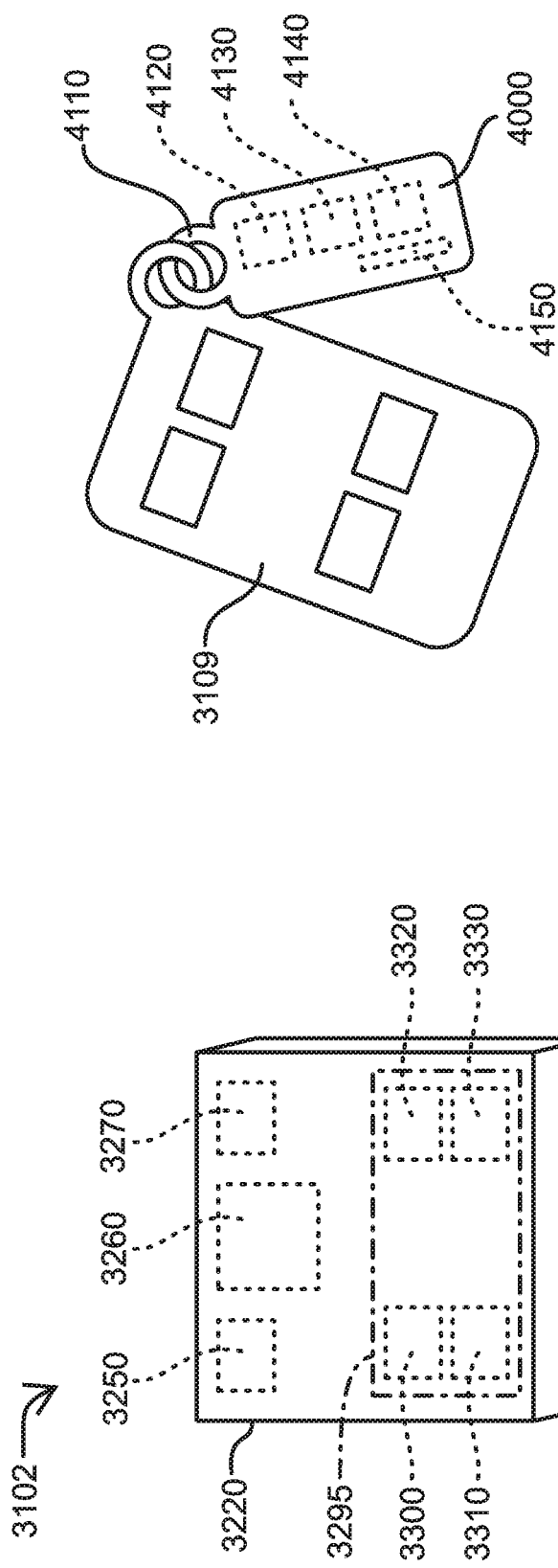

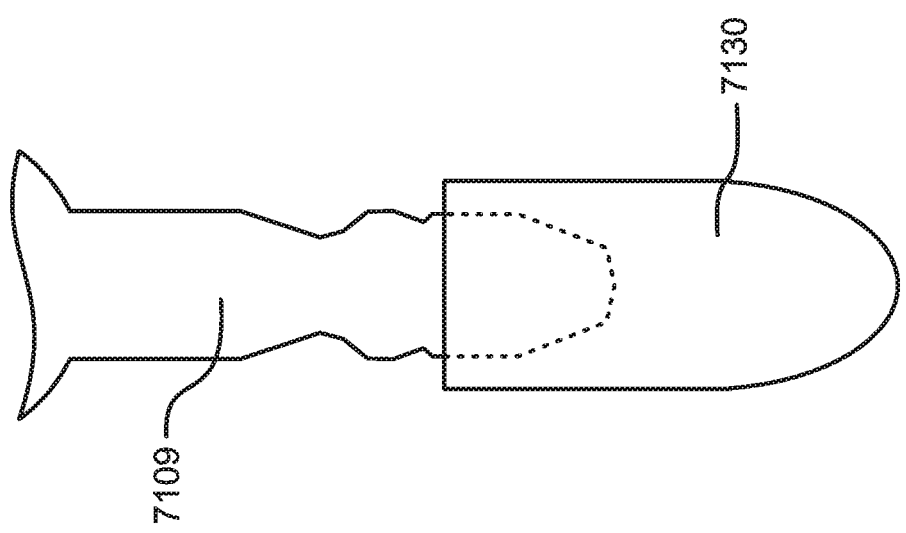

VEHICLE DRIVER MONITORING SYSTEM

CROSS-REFERENCE TO RELATED APPLICATIONS

This application claims the benefit of U.S. Provisional Application No. 62/293,195, filed Feb. 9, 2016, U.S. Provisional Application No. 62/350,289, filed Jun. 15, 2016, and U.S. Provisional Application No. 62/211,325, filed Aug. 28, 2015.

BACKGROUND

Driver safety is an issue of concern in the United States and many other countries. Over 30,000 people die due to fatal injuries caused by car accidents each year in the United States, with approximately ⅓ of the automobile fatalities being alcohol related.

Certain automobile monitoring devices are configured to limit or prevent a driver's access to a vehicle in the case where the driver is intoxicated. For example, conventional devices prevent operation of an automobile when an operator is impaired as a result of consumption of alcoholic beverages. These devices typically utilize a breath alcohol analyzer device which correlates the alcohol level in the user's bloodstream to the alcohol level in the user's breath. In the case where the breath alcohol analyzer device detects a blood alcohol level that is less than a predefined threshold, the device allows the user to start the automobile. By contrast, in the case where the breath alcohol analyzer device detects a blood alcohol level that is greater than a predefined threshold, the device prevents the user from starting the vehicle.

SUMMARY

Conventional automobile monitoring devices suffer from a variety of deficiencies. For example, conventional monitoring devices can prevent an operator from driving an automobile while intoxicated. However, driver intoxication represents only one possible cause of automobile accidents. In addition to alcohol-related driving fatalities, many drivers are killed or injured each year in automobile accidents, with speeding, texting, and non-hands-free phone use being the leading causes of accidents. Accordingly, while conventional automobile monitoring devices can prevent an operator from driving an automobile while intoxicated, these devices are not configured to detect or prevent other accident-prone behavior. Further, conventional monitoring devices are not configured to provide third-parties with notification regarding accident-prone behavior.

Additionally, conventional monitoring devices are configured as automobile-based driving prevention mechanisms. For example, conventional monitoring devices are not key-based methods of preventing driving but instead are configured to disable components of the automobile (e.g., ignition, alternator, etc.). The cost to retrofit an automobile with these conventional monitoring devices can be cost prohibitive for most.

By contrast to conventional automobile monitoring systems, embodiments of the present innovation relate to a vehicle driver monitoring system. In one arrangement, the vehicle driver monitoring system includes a supervisor computerized device in electrical communication with an operator computerized device. An optional key disabling device may also be included. The devices of the vehicle driver monitoring system work in conjunction with each other to optionally limit to the operability of a vehicle key and to monitor various aspects of the user's operation of a corresponding vehicle during use. For example, the supervisor computerized device is configured to remotely receive vehicle monitoring information, such as location information, speed information, and operator information, from the operator computerized device as the operator drives the vehicle. Further, the optional key disabling device may be configured to selectively allow operation of a vehicle key based upon one or more of access information, identity information, and sobriety information related to the user and as provided by the operator computerized device. Accordingly, the vehicle driver monitoring system gives a supervisor, such as a parent, the ability to track various aspects of the operation of the vehicle while preventing access to the vehicle when the operator, such as driver between ages of 16 and 22, is intoxicated.

BRIEF DESCRIPTION OF THE DRAWINGS

The foregoing and other objects, features and advantages will be apparent from the following description of particular embodiments of the innovation, as illustrated in the accompanying drawings in which like reference characters refer to the same parts throughout the different views. The drawings are not necessarily to scale, emphasis instead being placed upon illustrating the principles of various embodiments of the innovation.

FIGS. 9-12 illustrate a key disabling device of the vehicle driver monitoring system of FIG. 1, according to one arrangement.

FIGS. 19-22 illustrates wireless key disabling device of the vehicle driver monitoring system of FIG. 1, according to one arrangement.

FIG. 23 illustrates a wireless key disabling device of the vehicle driver monitoring system of FIG. 1, according to one arrangement.

FIGS. 28-30 illustrate a key disabling device of the vehicle driver monitoring system of FIG. 1, according to one arrangement.

DETAILED DESCRIPTION

Figure 1:
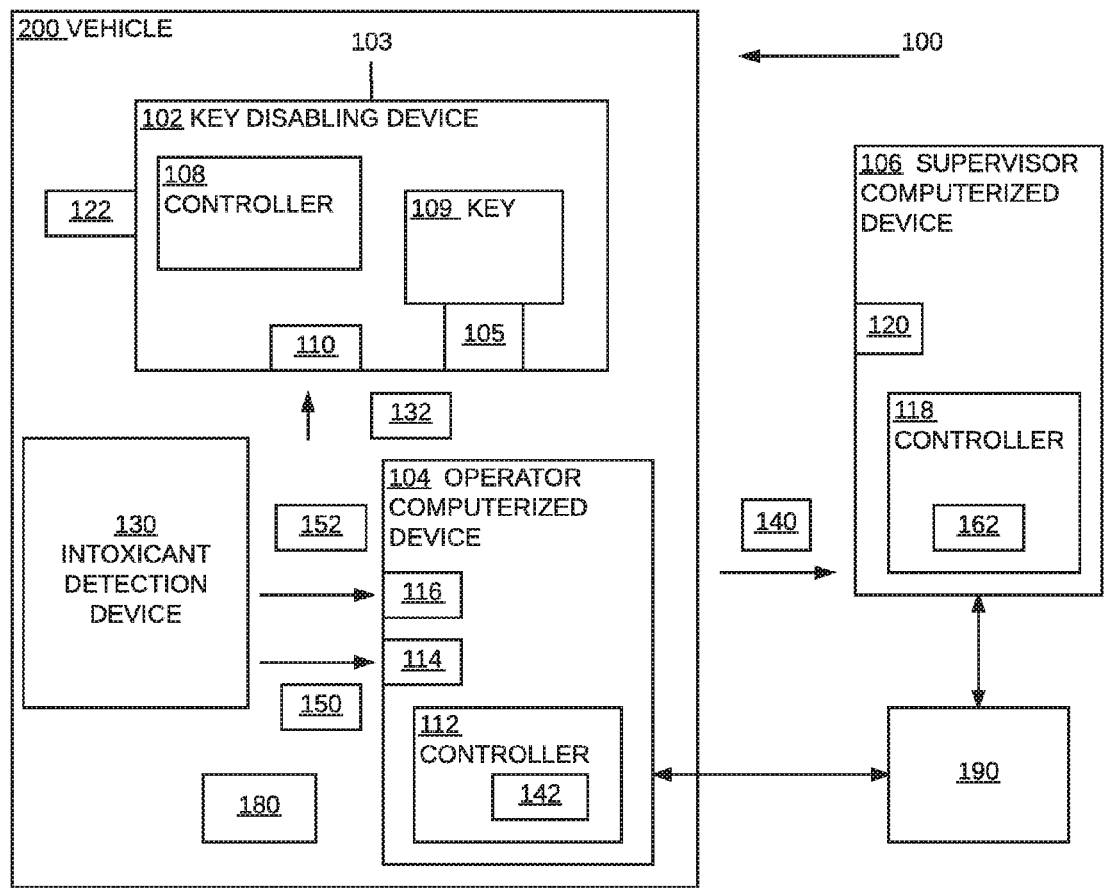
FIG. 1 illustrates a schematic representation of a vehicle driver monitoring system, according to one arrangement.

FIG. 1 illustrates a schematic representation of a vehicle driver monitoring system 100, according to one arrangement. As illustrated, the vehicle driver monitoring system 100 includes a key disabling device 102, an operator computerized device 104, and a supervisor computerized device 106. Each of the devices 102, 104, 106 are disposed in electrical communication with each other, such as via wireless communication. A variety of wireless communication modalities can be utilized among the devices 102, 104, 106 including Bluetooth and wireless communication protocols.

The key disabling device 102 is sized and shaped to be easily carried by a vehicle operator and to receive, and selectively allow an operator access to, a vehicle key. For example, the key disabling device 102 includes a housing 103 and a key securing mechanism 105 configured to couple a key 109 to the housing 103. The key securing mechanism 105 can be configured in a number of ways. For example, the key securing mechanism 105 can be configured as a spring-loaded key ring or clamp that secures the key 109 to the key disabling housing 103. Other examples of the key securing mechanisms 105 are provided and described in detail below.

In one arrangement, the key disabling device 102 includes a controller 108, such as a processor and memory. Based upon one or more identification signals received from the operator computerized device 104 via transceiver 110, the controller 108 is configured to selectively dispose a vehicle key 109 carried by the key disabling device 100 between being inoperable (i.e., such that an operator cannot use the key to activate a vehicle's ignition) and operable (i.e., such that an operator can activate the vehicle's ignition using the key). The disposition of the key 109 as being inoperable or operable can be performed in a variety of ways using a variety of mechanisms, as provided and described in detail below.

The operator computerized device 104 is configured to provide operator identification information 132 to the key disabling device 100 and vehicle monitoring information 140 to the supervisor computerized device 106. For example, the operator computerized device 104 can be configured as a smartphone, tablet device, or other computerized device having a controller 112, such as a processor and memory. As will be described in detail below, during operation the controller 112 executes an operator application 142 which configures the controller 112 to interact with the key disabling device 102 and the supervisor computerized device 106 via transceiver 116.

The operator computerized device 104 is further configured to receive operator identification information 150 which provides information regarding the identification of the operator. For example, the operator computerized device 104 can include a biometric identifier mechanism 114, such as a camera, fingerprint scanner, or retina scanner disposed in electrical communication with the controller 112. The biometric identifier mechanism 114 is configured to receive operator identification information 150, such as an image of the operator, or information about the operator's retina, for processing and verification (e.g., facial and/or video recognition) by the controller 112.

The operator computerized device 104 is also configured to receive operator sobriety information 152 which provides sobriety information related to the operator. In one arrangement, the operator computerized device 104 includes a transceiver 116 disposed in electrical communication with the controller 112 and configured to receive sobriety information 152 from an intoxicant detection device 130. For example, the intoxicant detection device 130, such as a breathalyzer device, provides information 152 related to the operator's level of an ingestible substance to the controller 112, such as via Bluetooth communication, for processing and verification. It is noted that the intoxicant detection device 130 can also be configured to detect the ingestion of variety of drugs by the operator.

In any of the disclosed embodiments of the present invention, a supervisor can choose whether the operator needs to pass a sobriety test. In addition, the supervisor can choose whether the operator needs to pass a facial recognition test or video confirmation test. The supervisor can alternatively choose that the operator does not need to pass either a facial recognition test or video confirmation test. In the case of video confirmation test, the supervisor is sent the video of the operator taking the sobriety test, and then has a certain amount of time during which the supervisor can verify the video. If the supervisor doesn't verify the video within a certain set time, which may be set by the supervisor, then the operator is free to operate the vehicle unless they receive a failed video identification notice from the supervisor. In that case, the operator would need to stop the vehicle and take the video recognition test and pass it and the sobriety test before they can continue to operate the vehicle.

The supervisor computerized device 106 is configured to receive vehicle monitoring information 140 from the operator computerized device 104. The vehicle monitoring information 140 relates to the operation of the vehicle by the operator and includes, e.g., speed or velocity information and location information, such as GPS coordinates. The supervisor computerized device 106 can be configured as a smartphone, tablet device, or other computerized device having a controller 118, such as a processor and memory. As will be described in detail below, during operation the controller 118 executes a supervisor application 162 which configures the controller 118 to interact with the operator computerized device 104 via transceiver 120.

Proximity sensor 180, which may be used to detect the presence of the operator in the vehicle, is securely attached somewhere in the vehicle. Alternatively, the proximity sensor 180 may be included in the intoxication detection device 130. When the proximity sensor 180 determines that the operator is in the vehicle, the sensor generates and sends a notification signal to the operator computerized device 104. In response to receiving the notification signal, the operator computerized device 104 may generate and transmit a signal to the key disabling device 102. The signal notifies the key disabling device 102 that the operator is in the vehicle 200 so that the key disabling device 102 can prevent operability of the vehicle key 109.

Database 190 is in electrical communication with both operator computerized device 104 and supervisor computerized device 106, and may be used to store any data relating the operator's use of the vehicle 200, the operator computerized device 104, the key disabling device 102, and the intoxicant detection device 130. Such data may include results of any identification tests and sobriety tests, vehicle monitoring information, images and/or video of the operator, etc. The database may also create reports of the operator's test results and driving habits.

During operation, the vehicle driver monitoring system 100 is configured to limit an operator's accessibility to a vehicle key and to monitor various aspects of the user's operation of a corresponding vehicle during use.

In an alternative embodiment, key disabling device 102 is not used. The supervisor can still require the operator to pass and identity and/or a sobriety test, but the operator's key will remain operable. In this embodiment, if the operator fails one of the tests, the supervisor will still be notified. In addition, monitoring information 140 is still received by the supervisor computerized device.

Figure 2:
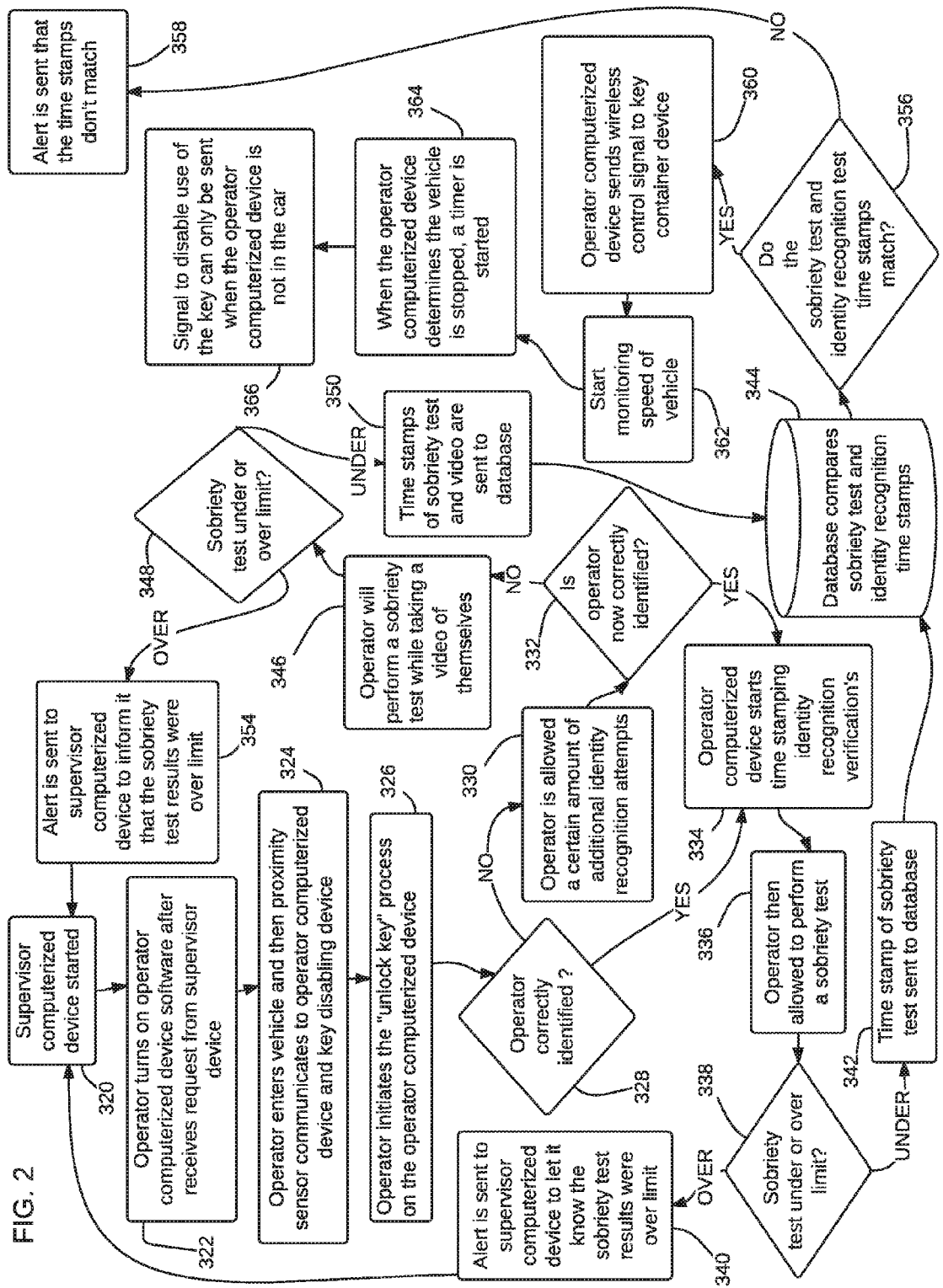
FIG. 2 is a flowchart illustrating an example of operation of the vehicle driver monitoring system of FIG. 1, according to one arrangement.
Figure 3:
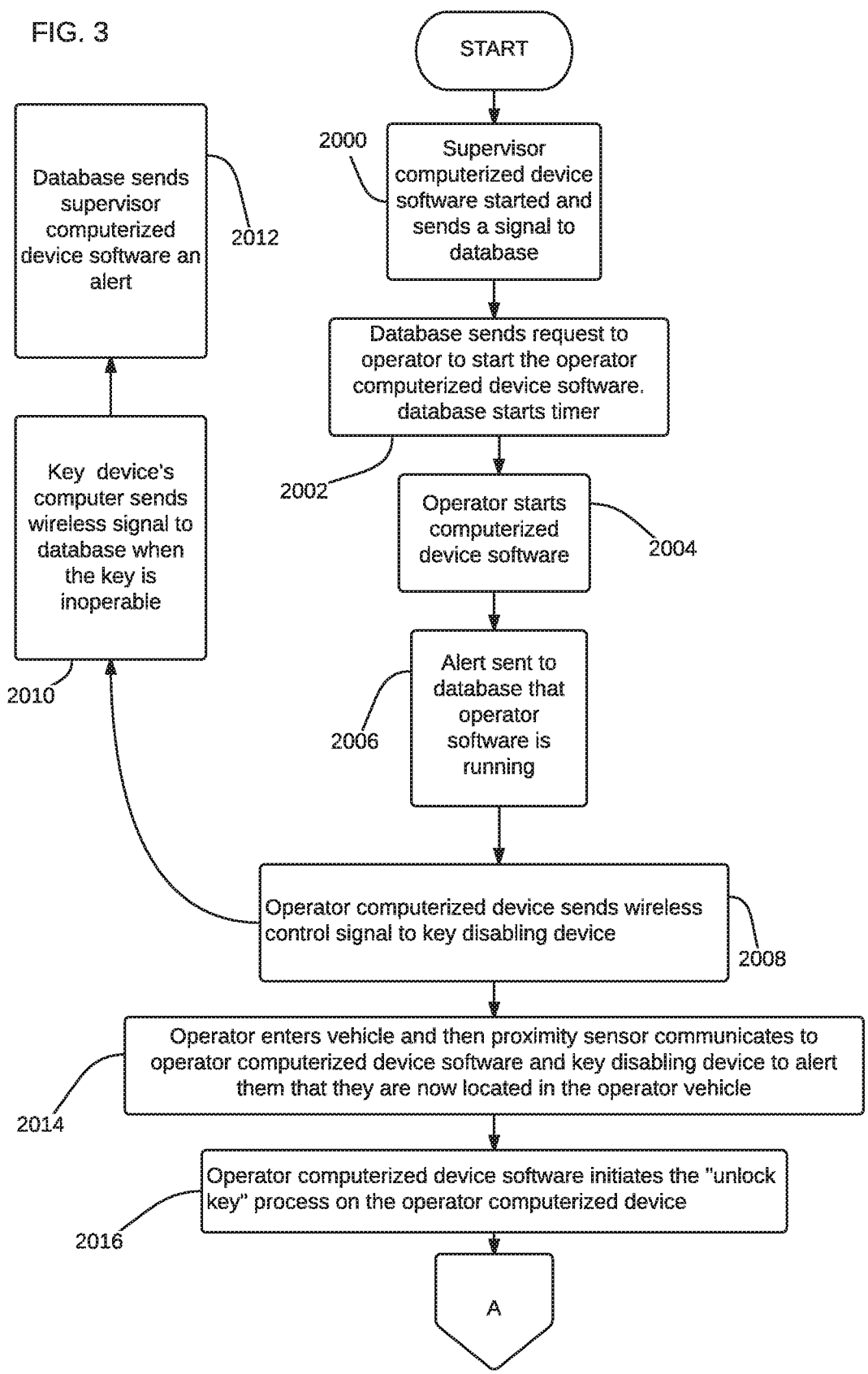
FIGS. 3-8 are flowcharts illustrating another example of operation of the vehicle driver monitoring system of FIG. 1, according to an alternative arrangement.
Figure 4:
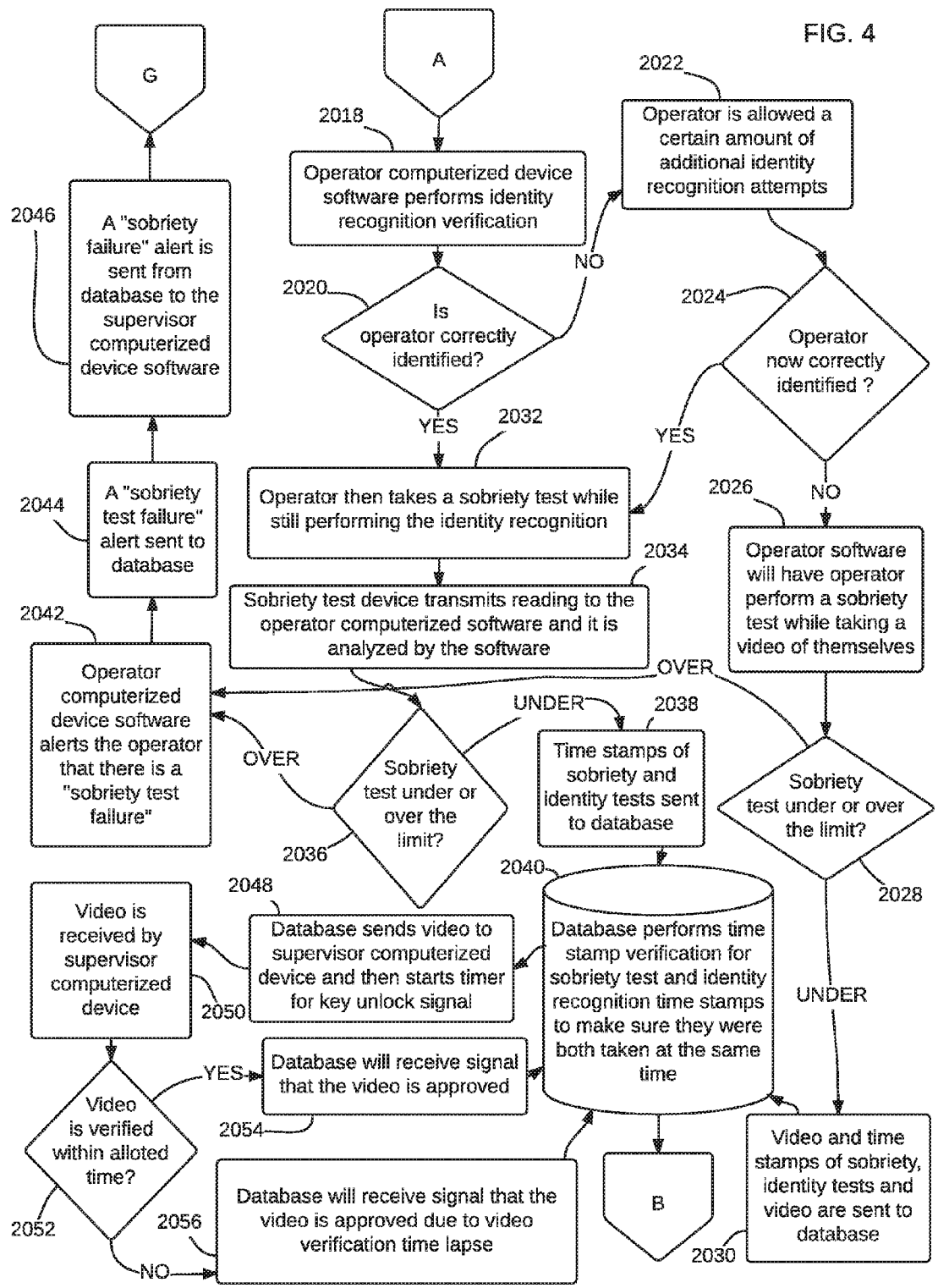
Figure 5:
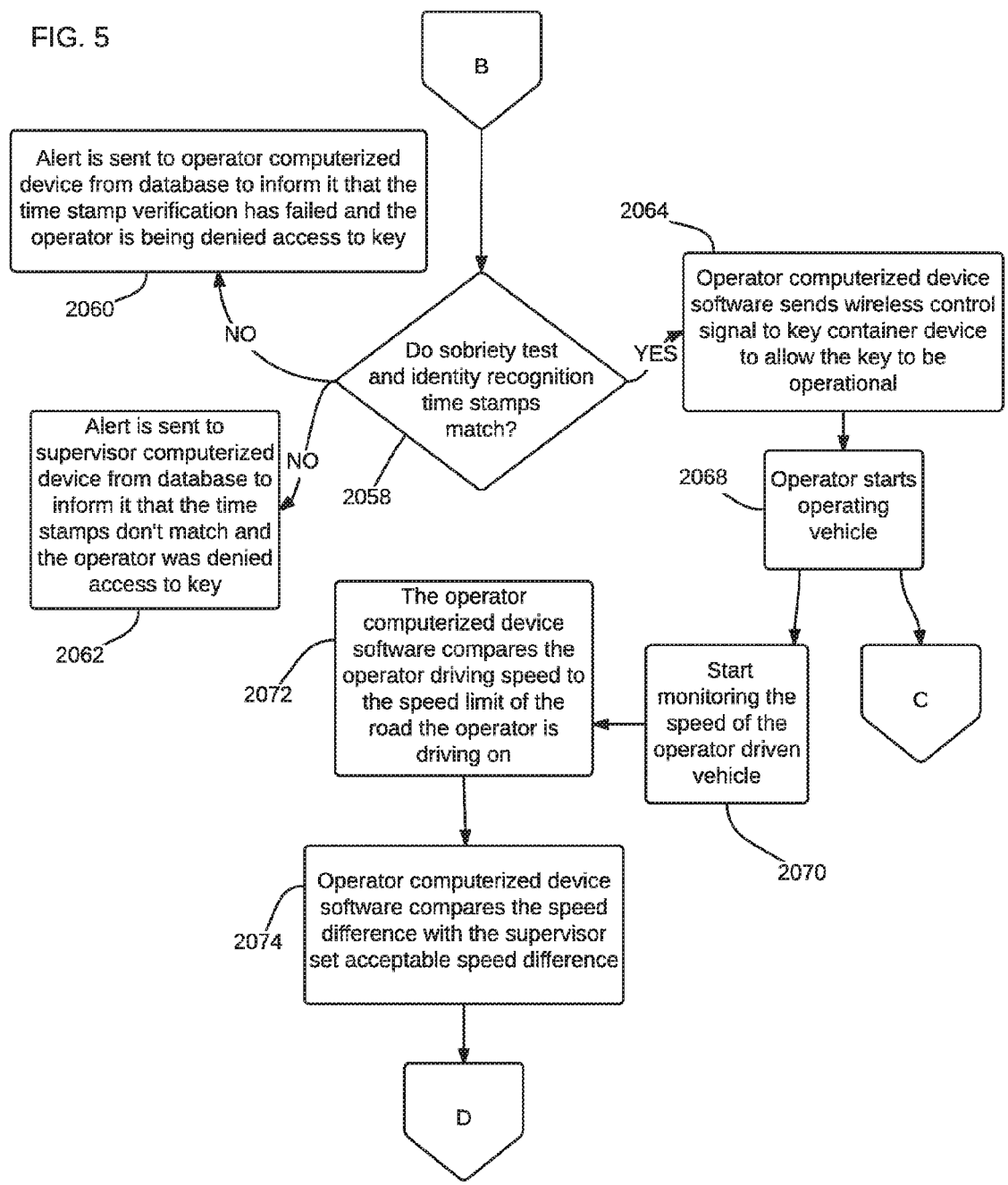
Figure 6:
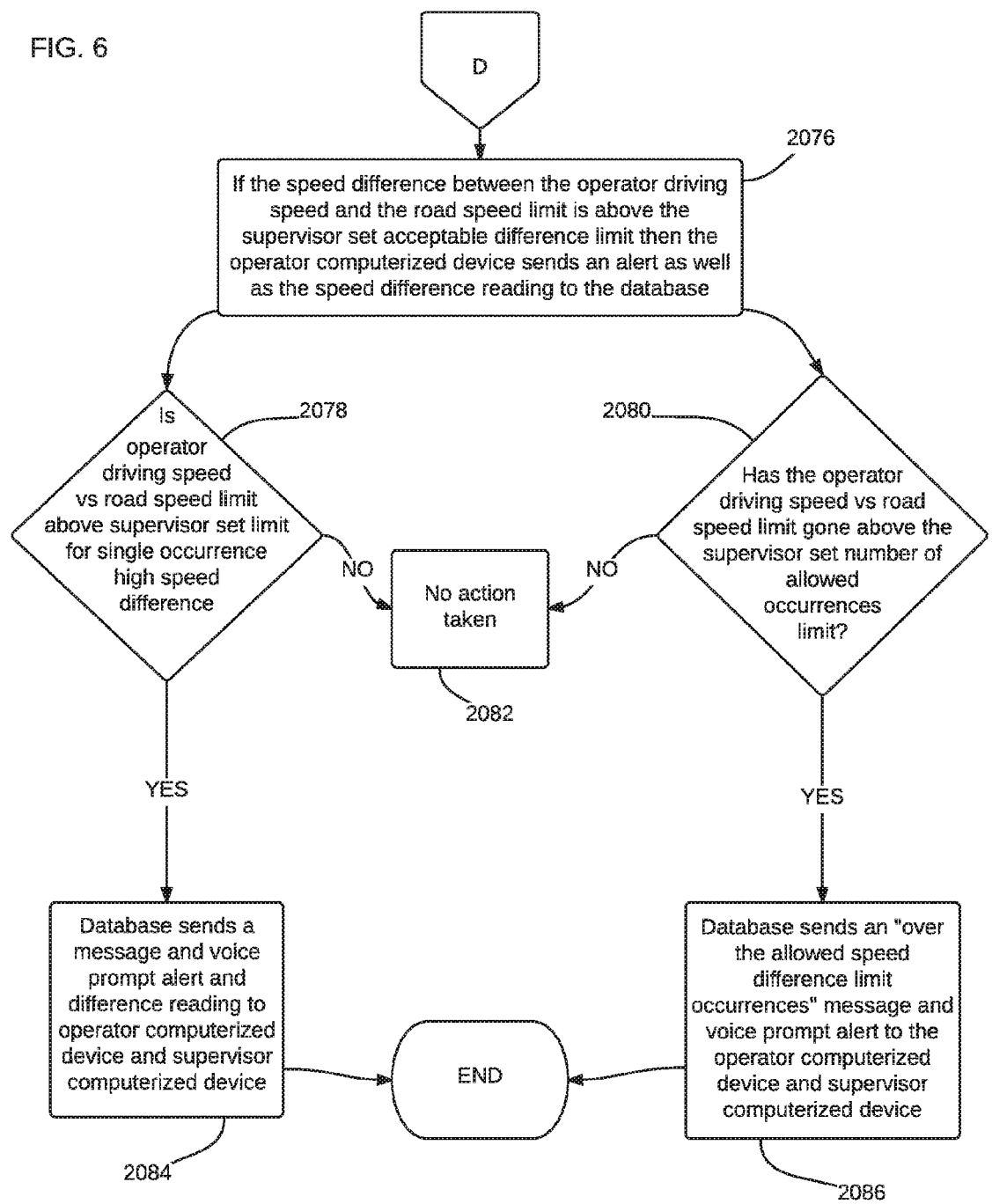
Figure 7:
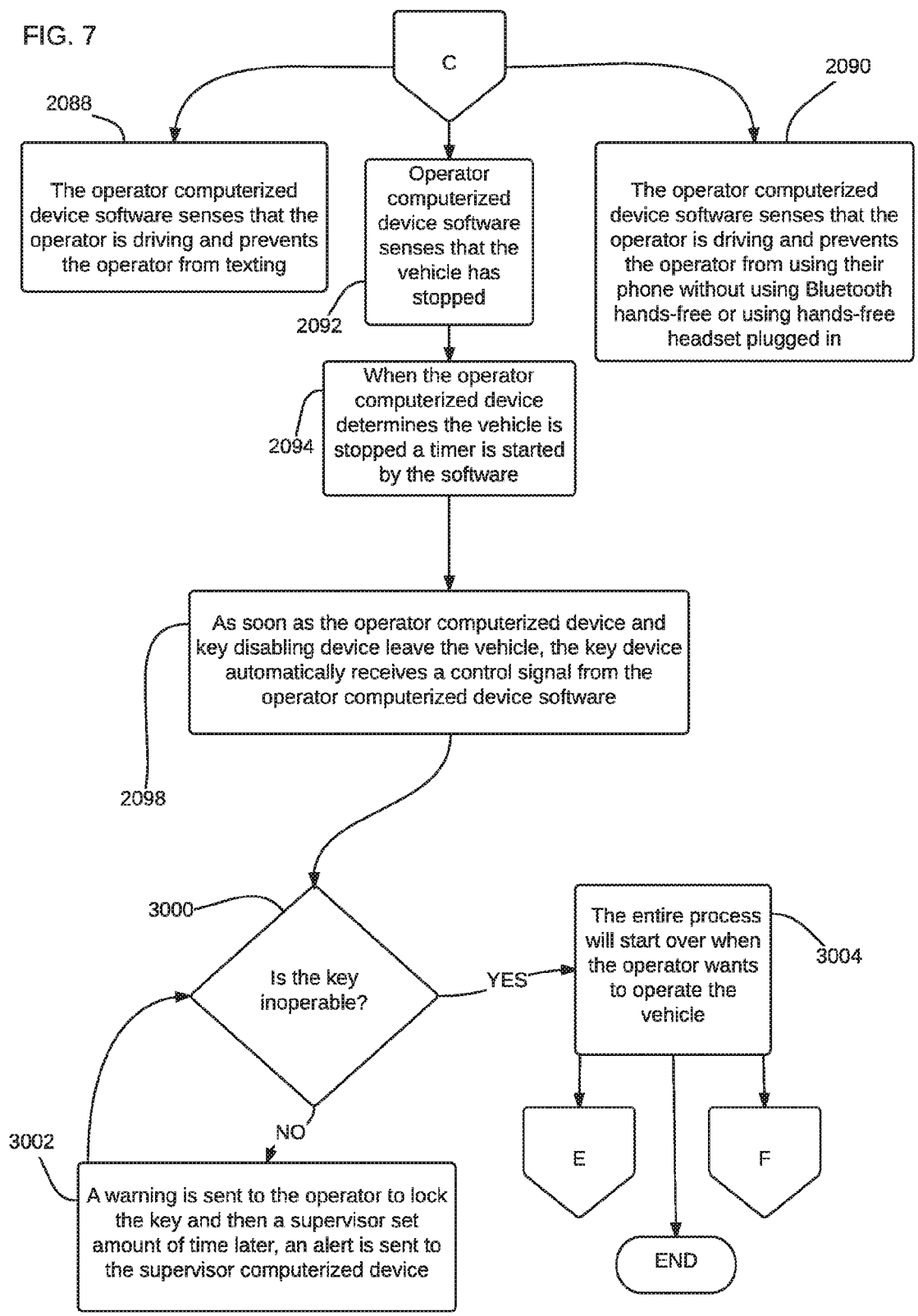
Figure 8:
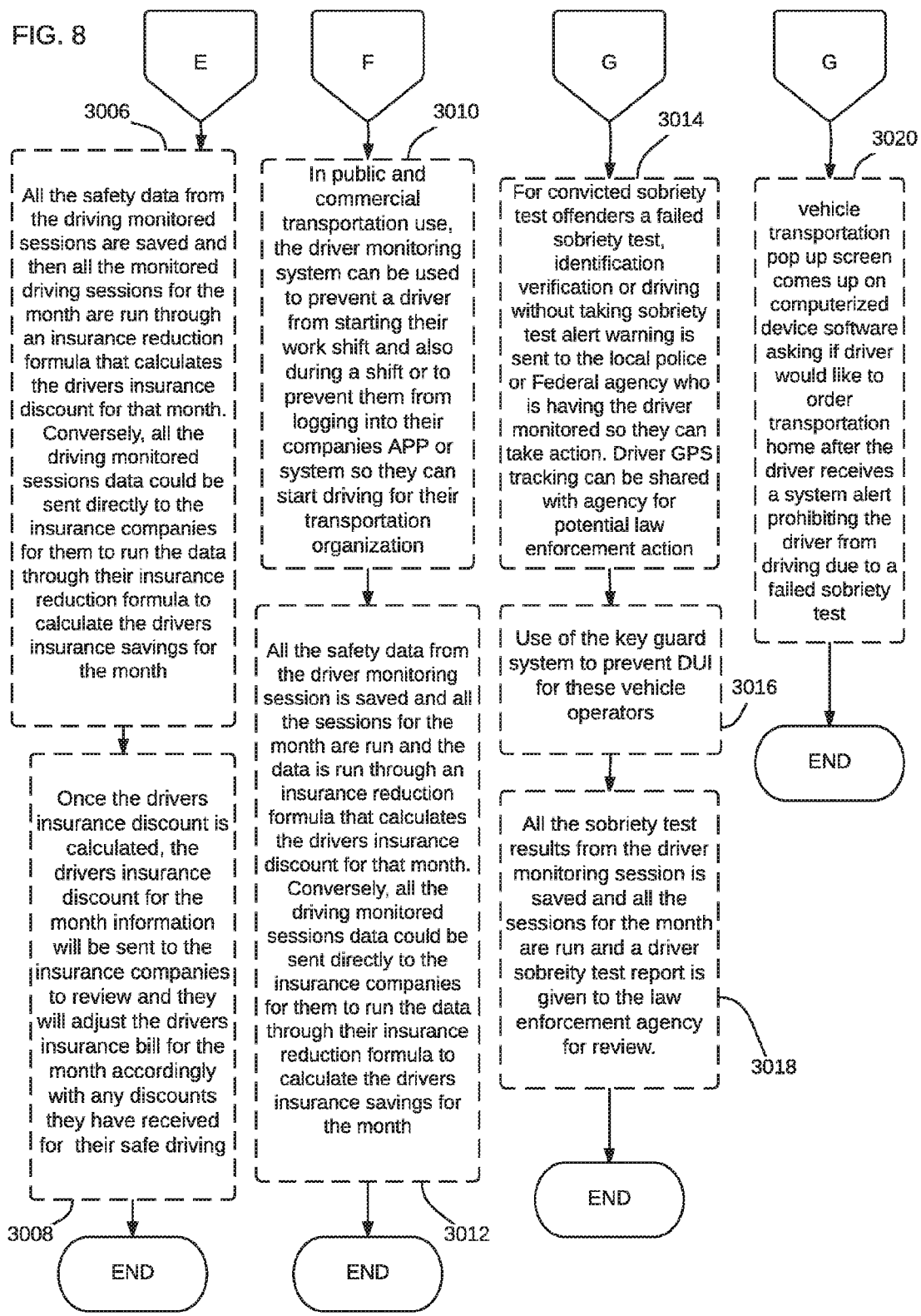

FIG. 2 illustrates one embodiment of a method according to principles of the present invention. Prior to the performance of the steps of this method, in one embodiment, a vehicle key 109 may have been secured in a key disabling device 102. In one embodiment, the vehicle key 109 may be a traditional key that is inserted into a lock. In an alternative embodiment, the vehicle key 109 may be a wireless key. In another alternative embodiment, the vehicle key 109 has not been secured in a key disabling device.

In order to secure the key 109 in the key disabling device 102, the supervisor activates the key disabling device 102 to insert and secure the key 109 thereto. For example, the supervisor can utilize the application 162 on the supervisor computerized device 106 to open the key disabling device 102 and allow access to the key securing mechanism 105. Once open, the supervisor can attach the key 109 to the key securing mechanism 105.

The methods described herein may make reference to disabling or preventing use of key 109. The specific means used to disable or prevent use of key 109 are described with reference to FIGS. 9-32, and may include, e.g., extending one or more security rods to prevent the insertion of the key 109 into the vehicle's ignition. In the embodiment where key 109 is a wireless key, the means to disable or prevent use of the key may include, e.g., a wireless signal jammer.

Returning to the method in FIG. 2, in step 320, the supervisor computerized device 106 is turned on by, e.g., a parent or a supervisor, and the supervisor application 162 is activated. For example, the supervisor can activate the application 162 on the supervisor computerized device 106 which, in turn, can cause the controller 118 to generate and transmit an activation signal to the operator computerized device 104, such as using a Bluetooth communication protocol via transceiver 120. The activation signal is configured to activate the operator application 142 on the operator computerized device 104 such that further communications can take place between the operator computerized device 104 and the key disabling device 102 and between the operator computerized device 104 and the supervisor computerized device 106.

In step 322, the operator computerized device 104 is turned on after receiving a request from the supervisor computerized device 106, and the operator application 142 is activated. Alternately, the supervisor can activate the operator application 142 directly on the operator computerized device 104 via a supervisor portal associated with the device 104 (i.e., either a hardware or software portal) using a particular supervisor control code.

In step 324, the operator enters the vehicle and the proximity sensor communicates to operator computerized device 104 that the operator is now located in the operator vehicle.

In step 326, the operator initiates a process on the operator computerized device 104 to make key 109 operable. This process requires the operator to pass two tests—a sobriety test and an identity recognition test. In the embodiment where the key 109 is not secured in a key disabling device 102, the process does not grant access to the key 109, but does inform the operator that he or she is authorized to operate the vehicle.

After the operator has initiated the process, a camera or other identity sensing device is activated to perform an identity test of the operator. In one embodiment, the camera captures a stream of images. In other embodiments, other identity information, e.g., biometric information, such as retina information, may be captured by the identity sensing device.

In step 328, the operator computerized device 104 determines, using the images or other identity information, if the operator is correctly identified, by facial recognition or another means.

If the operator is correctly identified in step 328, the method moves to step 334, where the time stamp of the identity recognition is saved in the database 190, and then to step 336, where the operator performs a sobriety test. The sobriety test may be a blood alcohol test, or may be a test testing another ingestible substance.

In step 338, it is determined if the operator's sobriety reading is over or under a previously set limit. This limit may have been previously set by the supervisor.

If the sobriety reading is over the limit, the method moves to step 340, where an alert may be sent to the supervisor computerized device, informing the device that the operator failed the sobriety test. In addition, the operator may be notified that he or she failed the sobriety test and that he or she is not authorized to operate the vehicle. In the embodiment where the key 109 has been secured in the key disabling device 102, the operator is not granted access to the key.

Returning to step 338, if the sobriety reading is under the limit set by the supervisor, the method proceeds to step 342, where the time stamp of the sobriety test is sent to the database and stored.

In step 344, the sobriety test time stamp and the identity recognition time stamp are compared to determine if both tests were performed contemporaneously. This is to help prevent the situation where one person takes and passes the identity recognition test, and then the operator computerized device 104 is handed to another person, who takes and passes the sobriety test.

In an alternative embodiment, the identity recognition test and the sobriety test may be performed at the same time, so the time stamp data is not stored or compared, and the operator is authorized to operate the vehicle and/or given access to the key 109, if it has been secured in the key disabling device 102, if the sobriety and identity recognition tests have been passed.

In step 356, if the time stamps are contemporaneous, the method proceeds to step 360, where the operator computerized device 104 sends a control signal to the key disabling device 102 to make the key operational. In the embodiment where the key 109 is a traditional vehicle key, and the means for preventing use of the key is a security rod, the security rod is retracted into the key disabling device. In the embodiment where the key 109 is a wireless key, a signal jammer may be disabled. An alert may be sent to the operator, indicating that the operator is authorized to operate the vehicle. In the embodiment where the key 109 is not secured in the key disabling device 102, only the alert may be sent, as the key 109 has not been secured.

Returning to step 356, if the time stamps are not contemporaneous, the method proceeds to step 358, where an alert is sent to the supervisor computerized device 106, informing the supervisor computerized device that the time stamps did not match and that the operator was not authorized to operate the vehicle.

After the operator has been authorized to operate the vehicle, and the operator has been given access to the key 109, in step 362, the system monitors the speed of the vehicle. In one embodiment, the operator computerized device 104 is able to, through GPS or other means, monitor the vehicle's speed.

In step 364, the operator computerized device 104 detects that the vehicle has been stopped. After it has been determined that the vehicle is stopped, e.g., the vehicle's speed is zero, a timer is started by the operator computerized device 104. The supervisor may have previously set a time limit that a vehicle is allowed to be stopped before the operator is required to take another test. After this amount of time has passed, in step 366, the operator computerized device 104 may signal the key disabling device 102 to prevent use of the key 109 by the operator, e.g., by extending a security rod or activating a signal jammer. In addition, the operator computerized device 104 will require the operator to take the identity recognition and sobriety tests again before the operator is authorized to operate the vehicle. Where a key disabling device 102 is not being used, the operator computerized device 104 will just require the operator to take the identity recognition and sobriety tests again.

Additionally, if the operator leaves the vehicle after the operator computerized device 104 has detected that the vehicle has stopped, the operator computerized device 104 will signal the key disabling device 102 to prevent use of the key 109 by the operator, e.g., by extending a security rod. In addition, the operator computerized device 104 will require the operator to take the identity recognition and sobriety tests again before the operator is authorized to operate the vehicle. Where a key disabling device 102 is not being used, the operator computerized device 104 will just require the operator to take the identity recognition and sobriety tests again.

Returning to step 328, if the operator is not correctly identified by the identity recognition test, the operator is allowed a pre-determined number of additional identity recognition attempts in step 330. The number of identity recognition attempts allowed may have been previously set by the supervisor.

In step 332, if the operator is now correctly identified, the method proceeds to step 334, as described above. Otherwise, the method proceeds to step 346.

In step 346, the operator performs a sobriety test as described above while videoing him or her-self with the operator computerized device. In step 348, it is determined, as described above with respect to step 338, if the operator's sobriety is over or under the limit. If the sobriety reading is over the limit, the method proceeds to step 354, where an alert may be sent to the supervisor computerized device, informing the device that the operator failed the sobriety test. In addition, the operator may be notified that he or she failed the sobriety test and that he or she is not authorized to operate the vehicle. In the embodiment where the key 109 has been secured in the key disabling device 102, the operator is not granted access to the key.

In step 350, if the operator's sobriety is under the limit, the video recorded by the operator is sent to the supervisor computerized device 106 and there is a pre-set amount of time in which the supervisor may verify the operator's identity. When the supervisor verifies the operator's identity or does not respond in the pre-set amount of time, the operator computerized device 104 sends a control signal to the key disabling device 102 to make the key operational. An alert may be sent to the operator, indicating that the operator is authorized to operate the vehicle. In the embodiment where the key 109 is not secured in the key disabling device 102, only the alert may be sent, as the key 109 has not been secured. In addition, the time stamps of the sobriety test and the identity recognition test are sent to the database for later analysis by the supervisor.

In any step of the method of FIG. 2, if the operator operates the vehicle without being authorized by the operator computerized device 104, an alert may be sent to the supervisor computerized device 106 indicating that the vehicle is being operated without authorization.

FIGS. 3-8 illustrate another embodiment of a process according to an aspect of the invention. Prior to the performance of the steps of this method, in one embodiment, a vehicle key 109 may have been secured in a key disabling device 102, as described above with reference to FIG. 2. Alternatively, the vehicle key 109 may not have been secured in a key disabling device 102.

In step 2000, the supervisor computerized device software is started and sends a signal to the database 190.

In step 2002, the database 190 sends a request to the operator computerized device 104 to start the operator computerized device software. The database 190 also starts a timer. At pre-determined intervals, e.g., every 10 minutes, the database 190 sends a notification to the operator computerized device 104 and the supervisor computerized device 106 indicating that the operator has not started the operator computerized device software.

In step 2004, the operator starts the operator computerized device software.

In step 2006, an alert is sent to the database indicating that the operator computerized device software has been started. In one embodiment, the database then receives a signal from the operator computerized device software a predetermined intervals, e.g., every 5 minutes or every 30 minutes, until the end of the driver monitoring session or the session is manually stopped by the supervisor. This is to prevent the operator from shutting off the operator computerized device software without the supervisor knowing. The supervisor then can take action to get the operator to turn back on the software. The operator software will receive an alert message that the supervisor software will be notified within a predefined number of minutes, e.g., 2 minutes, if they don't turn back on the software.

After the operator computerized device software has been started, the method proceeds to step 2008, where the operator computerized device 104 sends a signal to the key disabling device 102 to prevent the use of the key by the operator.

In step 2010, the key disabling device 102 sends a signal to the database when the key 109 is inoperable.

In step 2012, the database sends the supervisor computerized device 106 an alert that the key 109 is inoperable.

In step 2014, the operator enters the vehicle and the proximity sensor may communicate to the operator computerized device 104 and the key disabling device 102 that they are now located in the operator's vehicle.

In step 2016, the operator computerized device 104 initiates a process for allowing the operator use of the key 109. This process requires the operator to pass two tests—a sobriety test and an identity recognition test. In the embodiment where the key 109 is not secured in a key disabling device 102, the process does not grant access to the key 109, but does inform the operator that he or she is authorized to operate the vehicle.

In step 2018, after the operator has initiated the process, a camera or other identity sensing device is activated to perform an identity test of the operator. In one embodiment, the camera captures image information about the operator, e.g., an image, a stream of images, or a video of the operator. In other embodiments, other identity information, e.g., biometric information such as information regarding the operator's retina, may be captured by the identity sensing device.

In one embodiment, the operator computerized device 104 is configured to compare the image information captured by the camera with an operator image database to determine if the image received is that of the operator. The operator image database may be stored on one of the computerized devices or on a separate database server. In the case where the image information matches an image in the database, the operator computerized device 104 can detect that the correct operator is present and is using the intoxicant detection device 130. In the case where the image information does not match an image in the database, the operator computerized device 104 can detect that the correct operator is not using the intoxicant detection device 130.

In one arrangement, the operator computerized device 104 is configured to send the image information to the supervisor computerized device 106. This allows the supervisor to review the image information, in real-time or at a later time, to prevent unauthorized use, e.g., to make sure the operator is not blowing into a fake breathalyzer while their sober friend is blowing into the real one.

In step 2020, if the operator is correctly identified by identity recognition, the method proceeds to step 2032, where the operator takes a sobriety test while performing the identity recognition. While the operator is taking the sobriety test, the system may continue to capture image information of the operator or other identification information, and continues to verify the identity of the person taking the sobriety test.

For example, the operator can blow into an intoxicant detection device 130, such as a portable breathalyzer (e.g., a Bluetooth enabled breathalyzer) or a drug detection device configured to detect any of a number of substances while they hold the operator computerized device 104.

In step 2034, the sobriety test device transmits the measured reading to the operator computerized software.

In step 2036, the sobriety test reading is compared to a previously set sobriety threshold value. This sobriety threshold value may have been previously set by the supervisor. The operator computerized device 104 is configured to compare the sobriety test reading to the sobriety threshold value to determine if the operator is over or under the sobriety threshold. For example, the sobriety threshold value may be a blood alcohol content (BAC) of 0.02 The level of other substances may be tested, instead of or in addition to alcohol.

If the test reading is over the sobriety threshold value, the method proceeds to step 2042, where the operator computerized device software may alert the operator that there has been a sobriety failure, and that the operator is not authorized to operate the vehicle. The alert may display the sobriety reading vs. the sobriety threshold value. The alert may also inform the operator that the supervisor has been alerted of the sobriety test failure.

In step 2044, a sobriety failure alert, along with the sobriety reading, is sent to the database. In step 2046, a sobriety failure alert is sent to the supervisor computerized device. This alert may include the sobriety reading and the sobriety threshold value.

If, in step 2036, the test reading is under the sobriety threshold value, the time stamps of the sobriety and identity recognition tests are sent to the database in step 2038. Then, in step 2040, the database compares the time stamps of the sobriety and identity recognition tests to make sure they were taken contemporaneously. This is to help prevent the situation where one person takes and passes the identity recognition test, and then the operator computerized device 104 is handed to another person, who takes and passes the sobriety test.

In an alternative embodiment, the identity recognition test and the sobriety test may be performed at the same time, so the time stamp data is not stored or compared, and the operator is authorized to operate the vehicle and/or given access to the key 109 (if it has been secured in the key disabling device 102) if the sobriety and identity recognition tests have been passed.

If the time stamps are contemporaneous (step 2058), the method proceeds to step 2064.

In step 2064, the operator computerized device 104 sends a control signal to the key disabling device 102 to make the key operational. In the embodiment where the key 109 is a traditional vehicle key, and the means for preventing use of the key is a security rod, the security rod is retracted into the key disabling device. An alert may be sent to the operator, indicating that the operator is authorized to operate the vehicle. In the embodiment where the key 109 is not secured in the key disabling device 102, only the alert may be sent, as the key 109 has not been secured.

In step 2068, the operator starts operating the vehicle. If the operator hasn't begun operating the vehicle after a pre-determined amount of time, e.g., 5 minutes, the key may be rendered non-operational again. The pre-determined amount of time may have been previously set by a supervisor.

If the operator is not correctly identified by the identity recognition test performed in step 2020, the method proceeds to steps 2022 and 2024, where additional identity recognition attempts are allowed. The number of additional identity recognition attempts may have been previously set by the supervisor.

In step 2024, if the operator is now correctly identified, the method proceeds to step 2032, as described above. Otherwise, the method proceeds to step 2026.

If the operator cannot be identified, in step 2026, the operator performs a sobriety test as described above while taking a video of themselves.

In step 2028, it is determined, as described above with respect to step 2036, if the operator's sobriety is over or under the sobriety threshold value. If the sobriety reading is over the sobriety threshold value, the method proceeds to step 2042, as described above.

In step 2028, if the operator's sobriety is under the sobriety threshold value, the method proceeds to step 2030, where the video recorded by the operator is sent to the database, along with the time stamps of the sobriety and identity recognition test. The method then proceeds to step 2048, where the database sends the video to the supervisor computerized device and starts a timer. In step 2050, the video is received by the supervisor computerized device, and there is a pre-set amount of time in which the supervisor may verify the operator's identity. In step 2052, it is determined if the supervisor has verified the operator's identity. If so, in step 2054, the supervisor computerized device sends a signal to the database indicating that the video has been approved. The process then continues in step 2040, where the time stamps of the sobriety reading and the identity recognition are compared as described above. In step 2052, if the video has not been approved by the supervisor, but the pre-set verification time has elapsed, the video is approved in step 2056, and the process then continues in step 2040, where the time stamps of the sobriety reading and the identity recognition are compared as described above. Alternatively, the video may not be sent to the database, for example where the operator is not allowed to operate the vehicle unless the identity recognition test is passed, e.g., in a work-related or governmental environment where nobody is allowed to access the vehicle unless the identity recognition test is passed.

Returning to step 2058, if the time stamps of the sobriety test and the identity recognition test are not reasonably contemporaneous, the method proceeds to steps 2060 and 2062. In step 2060, an alert is sent to the operator computerized device, and the operator computerized device informs the operator that the time stamp verification was unsuccessful, and that the operator is not authorized to operate the vehicle. The operator computerized device may also inform the operator that the supervisor has been notified of the time stamp verification failure. In step 2062, an alert is sent to the supervisor computerized device that the time stamp verification was unsuccessful.

After the operator starts operating the vehicle, in step 2068, which may be detected using a GPS position device, an accelerometer, or any other means for identifying position or movement, the operator computerized device 104 is configured to detect various aspects of the operation of the vehicle 200, such as speed limit adherence, GPS location, and whether the vehicle has stopped. Further, the operator computerized device 104 can be configured to disable a texting feature and/or a phone feature of the operator computerized device while the operator is driving.

In one arrangement, the supervisor can set a speed limit threshold of the vehicle 200 associated with the operator computerized device 104. The threshold will determine the amount by which the operator can exceed the speed limit, e.g., by a certain miles per hour. The supervisor can also set a threshold for a number of times that the operator can exceed the speed limit before receiving a phone voice "slow down" warning. For example, the supervisor can set a limit of 20 miles per hour over the speed limit, where the numbers of times the operator can exceed the limit is only once before receiving a warning. As another example, the supervisor can set a limit of 5 miles per hour over the speed limit, where the numbers of times the operator can exceed the limit is four times before receiving a warning. The supervisor can set one or more of speed limit combined with occurrence thresholds. The speed limit information can be obtained from, e.g., a speed limit database.

In another arrangement, where the vehicle includes speed limiting functions, the speed limit thresholds can be communicated directly to the vehicle, and the vehicle can limit the operator's speed according to the supervisor's pre-set thresholds.

In one arrangement, during operation, the supervisor computerized device 106 is configured to receive vehicle monitoring information 140 in substantially real time from the operator computerized device 104 to track adherence to the speed threshold. This vehicle monitoring information 140 allows the supervisor to track the operator's speed during the course of a trip.

In one arrangement, the supervisor computerized device 106 is configured to receive vehicle monitoring information 140 in substantially real time from the operator computerized device 104 without activation of the key disabling device 102. With such a configuration the operator computerized device 104 actively shares information with the supervisor computerized device 106, without requiring the placement of a key 109 in the device 102. Accordingly, the operator computerized device 104 is configured to function as a tracking system. For example, during operation the operator computerized device 104 is configured to monitor operation (i.e., driving) of the vehicle. In one arrangement, the operator computerized device 104 can be further configured to create a log of all the activity of the operator and/or the number of times the driver went over the supervisor-set speed limits, as well as the amount over the speed limits. In this arrangement, the operator computerized device 104 can provide the vehicle monitoring information 140 as a report for later viewing, rather than in real time. Based on the vehicle monitoring information 140, the operator computerized device 104 can be configured to call or text the supervisor if the vehicle goes over a certain speed limit or goes over the speed limit a certain number of times. The log can be stored in database 190 or other data collection on any of the computerized devices, or on a separate database server.

In one arrangement, the vehicle monitoring information 140 can include location information that allows the supervisor to track the location of the vehicle 200. For example, the vehicle monitoring information 140 includes GPS information associated with the operator computerized device 104. As the operator computerized device 104 moves with the vehicle 200, a GPS device of the operator computerized device 104 provides GPS information to the supervisor computerized device 106. The supervisor computerized device 106 can display the GPS information as part of a map display to the supervisor.

In one arrangement, the operator computerized device 104 is configured to compare the generated GPS information with an address database. For example, the address database can include addresses where the operator is not allowed to travel. In the case where the operator computerized device 104 detects a match between the GPS information and the address database, the operator computerized device 104 may be configured to transmit an address warning to the supervisor computerized device 106. In another example, the address database can include geofence information which defines a perimeter in which the operator is allowed to travel. In the case where the operator computerized device 104 detects that the GPS information identifies a location that is outside of the geofence perimeter, the operator computerized device 104 is configured to transmit an address warning to the supervisor computerized device 106. The geofence can also be used when a driving curfew (i.e., 12 am-5:00 am) is in effect. If the vehicle is outside the operator's residence area (i.e., ¼ mile) then the operator will be allowed to access the vehicle and operate the intoxication detection device 130 so they can get home. If the vehicle is within the residential area geofence, then the operator can be denied access to the vehicle no matter if they are sober or not.

Returning now to the method of FIGS. 3-8, in step 2070, the operator computerized device starts monitoring the speed of the vehicle. In step 2072, the operator computerized device software compares the operator driving speed to the speed limit of the road the operator is driving on to calculate a speed difference.

In step 2074, the operator computerized device software compares the speed difference calculated in step 2072 with the supervisor-set acceptable speed difference. In step 2076, if the speed difference between the operator driving speed and the road speed limit is above the supervisor-set acceptable speed difference then the operator computer device sends an alert as well as the speed difference reading to the database.

The supervisor may have previously set speed difference rules. These rules would have the database send an alert and speed reading to the operator computerized device 104 and supervisor computerized device 106 when the speed difference is above a predetermined level (e.g., over 20 mph speed difference) or after the speed difference has gone above a supervisor-set mph difference a certain number of times (e.g., over 10 mph speed difference 3 different times).

In step 2078, the database determines if the operator driving speed is over the road speed limit by an operator-set limit for a single occurrence high speed difference. If not, the method proceeds to step 2082, where no action is taken. If yes, the method proceeds to step 2084, where the database may send an alert to either or both of the operator computerized device 104 and the supervisor computerized device 106. The alert may include any of: a message, a voice prompt alert, and the difference reading. A report with this information may also be generated by the database. This report may be accessible through the supervisor software (or other outside vendor software) for review.

In step 2080, the database determines if the operator driving speed is over the road speed limit by a supervisor-set limit for a number of occurrences. If not, the method proceeds to step 2082, where no action is taken. If yes, the method proceeds to step 2086, where the database may send an alert to either or both of the operator computerized device 104 and the supervisor computerized device 106. The alert may include any of: a message, a voice prompt alert, and the difference reading. A report with this information may also be generated by the database. This report may be accessible through the supervisor software (or other outside vendor software) for review.

With respect to the prevention of texting, in step 2088, the operator computerized device software senses that the operator is driving and may prevent the operator from using the operator computerized device 104 for texting. The operator has already had their identity verified by the operator software to be the vehicle driver, so there is no need have the software ask if the operator is driving the vehicle as is typical in other non-texting while driving solutions.

With respect to the prevention of use of the phone, in step 2090, the operator computerized device software senses that the operator is driving and may prevent the operator from using the operator computerized device 104 for making phone calls without using wireless hands-free or using hands-free headset plugged into phone. The operator has already had their identity verified by the operator software to be the vehicle operator, so there is no need to have the software ask if the operator is driving the vehicle.

With respect to the vehicle stopped process, in step 2092, the operator computerized device software senses that the vehicle has stopped. A lack of change in GPS information and/or an accelerometer can be used to determine if the vehicle has stopped moving. For example, after the operator has arrived at his destination, the operator places the vehicle 200 in park and will typically turn the vehicle ignition off.

In step 2094, a timer is started by the operator computerized device software. There is a pre-set amount of time, which may have been previously set by the supervisor, that the vehicle is allowed to be stationary without the operator having to take another sobriety/identity recognition test.

In step 2098, the operator computerized device 104 detects that the operator has left the vehicle. The operator computerized device 104 may detect this through the use of a proximity sensor or a GPS device. When the operator leaving the vehicle is detected, the operator computerized device signals the key disabling device 102 to prevent use of the key 109. Alternatively, the key disabling device 102 may detect that the operator has left the vehicle, and may prevent use of the key 109 without needing to be signaled by the operator computerized device 104.

In step 3000, it is detected if the key disabling device 104 is preventing use of the key 109. If yes, the process will start over when the operator wants to operate the vehicle (step 3004). If not, a warning is sent to the operator computerized device 104, and, a supervisor-set amount of time later, an alert is sent to the supervisor computerized device 106.

Optional steps 3006 and 3008 relate to an embodiment where the safety data from the monitored driving sessions is used to calculate an insurance discount for the operator.

In step 3006, all of the safety data from the monitored driving sessions are saved and then all the safety data are run through an insurance reduction formula that calculates the driver's insurance discount for that month. In addition to monitoring speed, as discussed above, the system may monitor use of seatbelts, the sending of texts, when calls are placed, etc. All of this safety data may be used in the calculation of an insurance discount. An insurance discount may be given for, e.g., the use of seat belts, lack of texting while driving, and hand-free calling.

In step 3008, once the driver's insurance discount is calculated, the driver's insurance discount for the month information will be sent to the insurance companies to review and they will adjust the driver's insurance bill for the month accordingly with any discounts they have received for their safe driving. Alternatively, all the monitored driving sessions' data may be sent directly to the insurance companies for them to run the data through their insurance reduction formula to calculate the driver's insurance savings for the month.

Optional steps 3010 and 3012 relate to an embodiment where the system is used by commercial or public entities.

In step 3010, in public and commercial transportation use, the driver monitoring system can be used to prevent drivers from operating their vehicle outside of their work shift. The system can tie into a timeclock system, to automatically know when the driver is authorized to use the vehicle. In such a system, after the driver passes the identity recognition and sobriety tests, the driver can be automatically clocked in.

The system can also be used to prevent drivers from logging into their company software or system so they can start driving for their transportation organization until they have passed the identity recognition and sobriety test. This may be used, e.g., for companies such as Uber and, Lyft, and the system disclosed herein may be incorporated into the company's internal application. The identity recognition and sobriety tests may be incorporated into the login process, or may be a standalone application.

In step 3012, all of the safety data from the monitored driving sessions are saved and then all the safety data are run through an insurance reduction formula that calculates the driver's insurance discount for that month. Alternatively, all the monitored driving sessions' data may be sent directly to the insurance companies for them to run the data through their insurance reduction formula to calculate the driver's insurance savings for the month.

Optional steps 3014, 3016, and 3018 relate to an embodiment where the driver is being monitored by an enforcement agency, such as a DUI Agency.

In step 3014, for convicted sobriety test offenders, a failed sobriety test, identification verification, or driving without taking sobriety test alert warning is sent to the local police or Federal agency that is having the driver monitored so they can take action. Driver GPS tracking can be shared with the agency for potential law enforcement action.

In step 3016, the system, including a key disabling device 102 that prevents use of a key 109 without passing the identity recognition and sobriety tests, may be used to prevent operators being monitored by an enforcement agency from driving under the influence.

In step 3018, all the sobriety test results from the driver monitoring sessions are saved and all the sessions for the month are run and a driver sobriety test report is given to the agency.

Optional step 3020 relates to an embodiment where the system calls a car service if the operator fails a test.

In step 3020, a vehicle transportation pop up screen comes up on operator computerized device 104 asking if the operator would like to order transportation home after the operator fails a sobriety test or fails the identity recognition test multiple times and has been prevented from operating the vehicle.

The above methods can be used in an embodiment where the key 109 is not secured in a key disabling device 102, and where the operator is allowed use of the key 109. In this embodiment, use of the key 109 is not prevented by the system; however, the operator must still pass the identity recognition and sobriety tests before receiving a notice that he or she is allowed to operate the vehicle. This is considered to be an "honor" system. If the operator operates the vehicle without passing the identity recognition and sobriety tests, an alert may be sent to the database 190 and/or the supervisor computerized device 106 indicating that the operator is operating the vehicle without authorization. This alert may be stored in the database and/or the supervisor computerized device 106 for later review.

Accordingly, the vehicle driver monitoring system 100 gives a supervisor, such as a parent, the ability to track various aspects of the operation of the vehicle while preventing access to the vehicle when the operator is intoxicated.

In the above methods, if the key 109 is a wireless key, the signal jamming that prevents operability of the key may only be activated when the operator enters the vehicle, and the signal jamming is deactivated when the operator passes the required tests. In this embodiment, when the vehicle is stopped, the signal jamming may be activated again.

As an additional option, the supervisor can send test notification alerts to the vehicle operator to have him or her take the identification and sobriety tests. This can be done manually by the supervisor, or the supervisor can have a notification alert sent at predetermined intervals, e.g. every 30 minutes or every 2 hours. The supervisor is notified if the operator doesn't take the tests or fails the tests. This may aid a supervisor who want to limit the operator's consumption of alcohol or other substances, regardless of whether or not the operator is operating the vehicle.

In one arrangement, the operator computerized device 104 is configured to first determine if the operator can access the key based upon preconfigured access information associated with the operator. For example, the operator computerized device 104 may perform an access time query to detect if the operator has access to key 109. For example, the operator may not be permitted access to the key 109 if the operator is grounded, it is past curfew, the operator is outside a defined geofence, etc. As another example, if the operator is a truck driver driving for a shipping company, the truck driver may not be allowed access to the truck until a shift start for them or if the company wants to terminate the driver, access to the driver's key may be blocked). If the operator computerized device 104 detects that the operator does not have access to the key 109 based upon the access time query, geofence query, etc., the operator computerized device 104 does not permit further access to the key 109.

In one embodiment, detection of movement of the vehicle 200 by the operator computerized device 104, e.g., through the use of a GPS device, accelerometer, or other means of detecting movement or location, configures the operator computerized device 104 to require the identification and sobriety tests described above. This feature allows the operator to not have to take the identification and sobriety tests after the supervisor enables the vehicle driver monitoring session 100 before, e.g., the operator leaves their own home for the night. The operator computerized device 104 would not start requiring testing until after the operator started driving to their initial destination and stopped the vehicle 200.

In one embodiment, when the proximity sensor 180 detects the presence of the operator, it can send a signal to the operator computerized device 104 or the supervisor computerized device 106 to start the monitoring of the driver speed, etc. This can be important in the situation where, for example, an insurance company wants to make sure that every time the operator uses the vehicle that driver safety information, including speed, is monitored. This can also be used to prevent the operator from texting and non-hands free phone use while operating the vehicle.

In one embodiment, the system includes a number of safety features. For example, the system may search local weather where the operator is located to make sure the weather will not go below a certain temperature, to prevent injury to the operator if the key disabling device 102 fails and the operator can't start his or her car in freezing weather when the key 109 has been made inoperable. As another example, the system may search a directory of people, e.g. a white pages directory, to make sure the number of houses nearby to where the driver is parking and the key disabling device 102 will be engaged is above a pre-set threshold. This helps ensure that if the key disabling device 102 fails, the operator can go to someone's house for help. As a further example, the system may the key 109 from becoming inoperable if there is no cell service where the operator is located, to prevent the operator from being unable to call for help.

As indicated above, the key disabling device 102 can be configured in a variety of ways. The configuration of the key disabling device 102 can depend upon the type of vehicle key used by the vehicle. For example, the key 109 can be configured as a mechanical key that physically interacts with the ignition of the vehicle. The following provides example embodiments of the key disabling devices 102 for mechanical ignition keys 109. In the following figures, some components may not appear in all drawings for ease of understanding.

FIGS. 9-12 illustrate one embodiment of a key disabling device. As illustrated, the key disabling device 9102 is configured as a lock box that goes around the bow (part you hold to use) of the key 9109. FIG. 9 illustrates a front view of the key disabling device 9102, which may include a window 9180. In use, the supervisor places the operator's key 9109 into the key disabling device. After the key disabling device 9102 is closed by the supervisor and locked, the operator can access some key functions (unlock/lock, etc.) through the window 9180. The window 9180 can be open air or can be covered with a plastic, mesh, or other material. An optional air bladder may be used to hold the key 9109 in place. The air bladder is filled and deflated through an air pump hole. As an alternative to an air bladder, foam may be used. As a further alternative, neither an air bladder nor foam may be used on the sides of the key 9109 to hold it in place.

CPU module 9250 is the central processing unit, and may be powered by battery module 9260. Wireless communication module 9270 allows for wireless communication with other components of the system, including, e.g., operator computerized device 104. In one embodiment, the security rod 9210 may be configured as a non-teethed rod that is pushed out and pulled in by motor 9290. Alternatively, the security rod 9210 may be configured as a teethed metal rod that is positioned relative to the key disabling device 9102 by gears. Other positioning mechanisms, as would be understood by one of ordinary skill in the art, may also be used.

FIG. 10 illustrates a view of the key disabling device 9102 in an open configuration of the back of the device. FIG. 10 shows the key disabling device 9102 without a key, whereas FIG. 9 shows the key disabling device 9102 after a key 9109 has been inserted. Hinges 9140, shown in FIG. 10, allow device 9102 to be opened, enabling the insertion of the key 9109 into the key disabling device 9102. Optionally, the key 9109 may be inserted into a key ring, After the key 9109 has been inserted into the key disabling device 9102, back door side 9165 and main key holder side 9170 may be swung together using hinges 9140 and latched or locked together using latch/lock parts 9150 and 9160. Optional stick on foam bumpers may be used to hold the key 9109 in place. As an alternative, foam may not be used to hold the key 9109 in place.

FIGS. 11-12 illustrate various CAD views of the key disabling device 9102.

Figure 13:
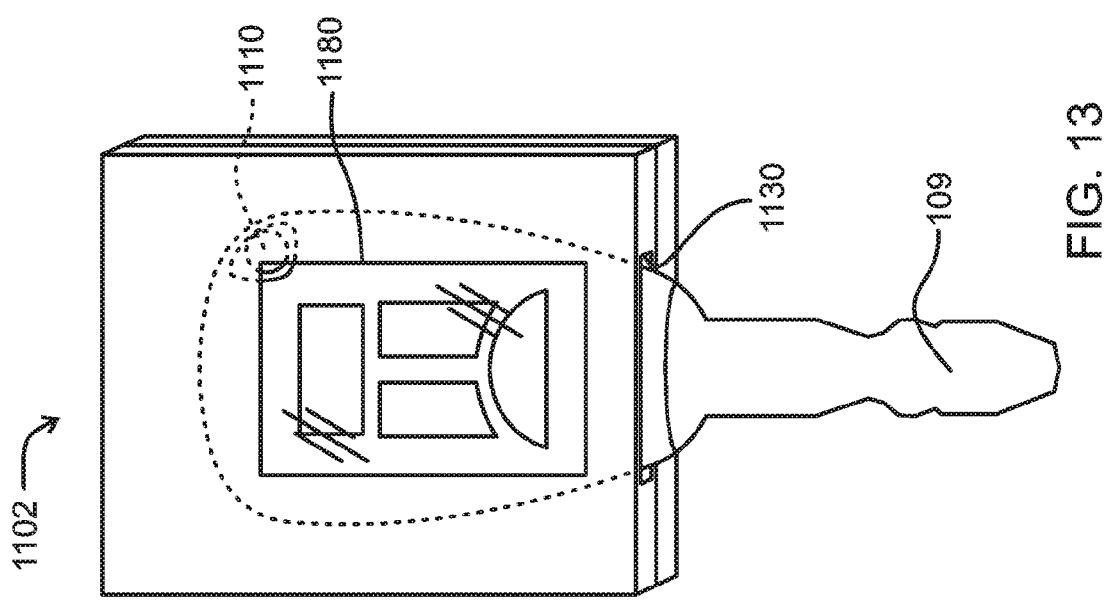

FIGS. 13-17 illustrate an alternative arrangement of a key disabling device. As illustrated, the key disabling device 1102 is configured as a lock box that goes around the bow (part you hold to use) of the key 109. FIG. 13 illustrates a front view of the key disabling device 1102, which may include one of more of the following: an adjustable and lockable overlapping key ring 1110, an opening 1130, and a window 1180. In use, the supervisor slides the operator's key 109 through the opening 1130 and locks the key 109 into the key ring 1110. The key ring 1110 may use a clamp lock or may be electronically locked. After the key disabling device 1102 is closed by the supervisor and locked, the operator can access some key functions (unlock/lock, etc.) through the window 1180. The window 1180 can be open air or can be covered with a plastic, mesh, or other material. Opening 1130 may include stretchable rubber or another flexible substance that helps to hold the key in place.

Figure 14:
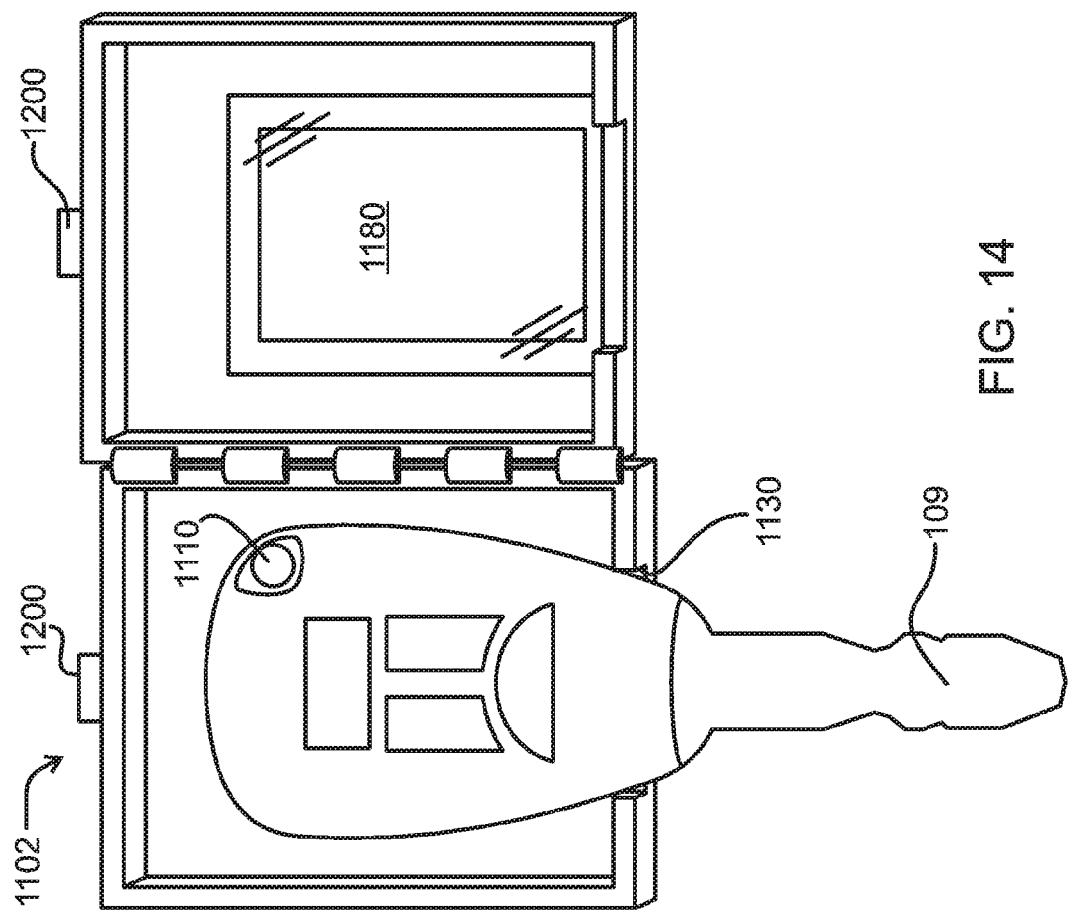
FIGS. 13-17 illustrate a key disabling device of the vehicle driver monitoring system of FIG. 1, according to one arrangement.
Figure 15:
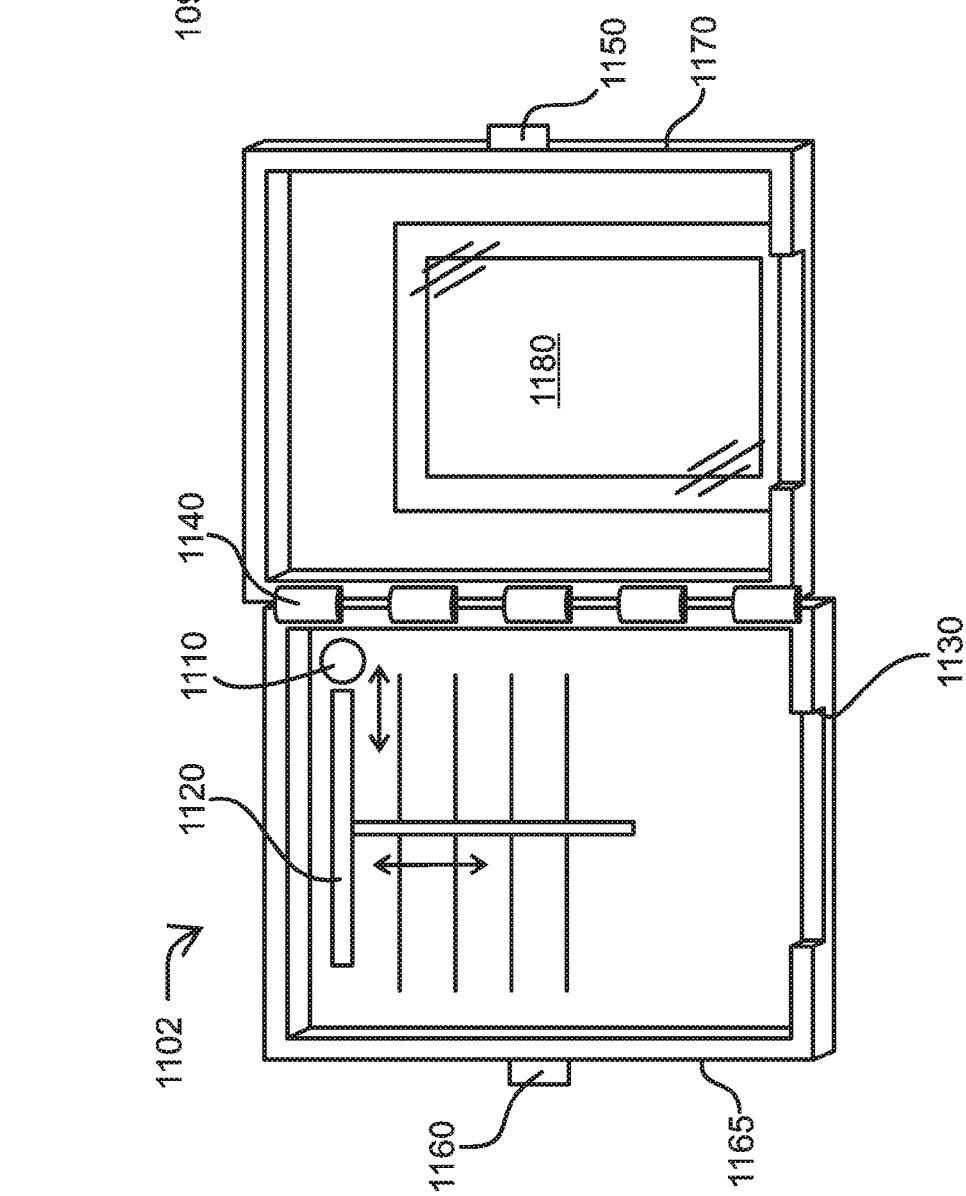

FIGS. 14 and 15 illustrate views of the key disabling device 1102 in an open configuration. FIG. 15 shows the key disabling device 1102 without a key, whereas FIG. 14 shows the key disabling device 1102 after a key 109 has been inserted. Hinges 1140, shown in FIG. 15, allow device 1102 to be opened, enabling the insertion of the key 109 into the key ring 1110 on key side 1165. Key track 1120, shown in FIG. 15, may be used to enable the key 109 to move to accommodate different key sizes and key ring placements. The key track 1120 enables the key ring 1110 to move to any location needed on key side 1165 to accommodate various sizes and placements of the key ring hole on the key 109. After the key 109 has been inserted into the key ring 1110, key side 1165 and window side 1170 may be swung together using hinges 1140 and latched or locked together using latch/lock parts 1150 and 1160. An optional air bladder may be used to hold the key 109 in place. The air bladder is filled and deflated through air pump hole 1200. As an alternative to an air bladder, foam may be used. As a further alternative, neither an air bladder nor foam may be used on the sides of the key 109 to hold it in place.

Figure 16:
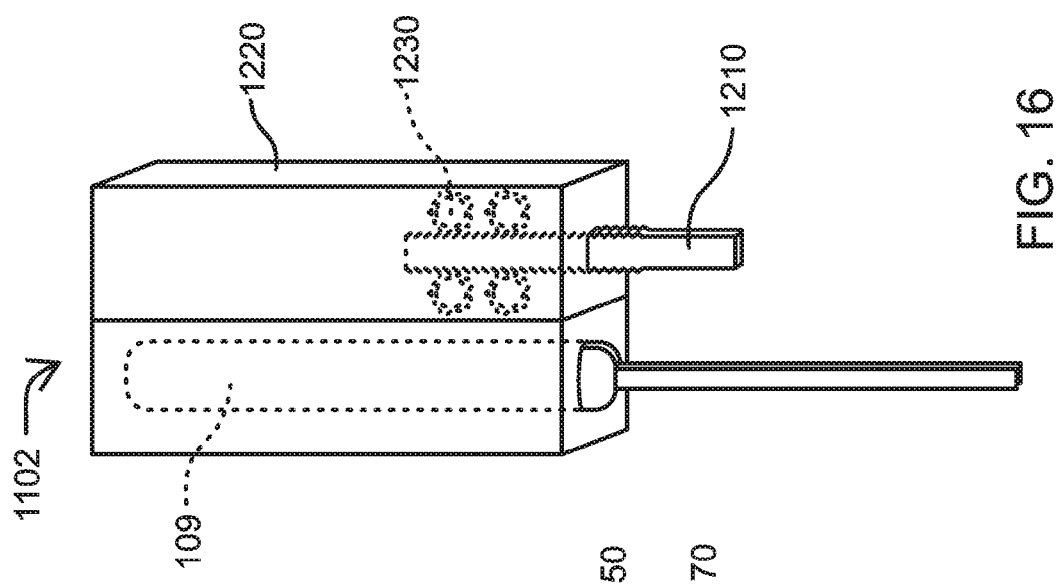

FIG. 16 illustrates a side view of the key disabling device 1102. FIG. 16 shows that the key disabling device 1102 may comprise two parts, a key holder part (which comprises key side 1165 and window side 1170) and a control box 1220.

The control box 1220 controls the positioning of a security rod 1210 to either allow or prevent the key 109 from being inserted into the ignition. The security rod 1210 may be configured as a teethed metal rod that is positioned relative to the key disabling device 1102 by gears 1230. Alternatively, the security rod 1210 may be configured as a non-teethed rod that is pushed out and pulled in by motor 1290, without using gears 1230. Other positioning mechanisms, as would be understood by one of ordinary skill in the art, may also be used.

Figure 17:
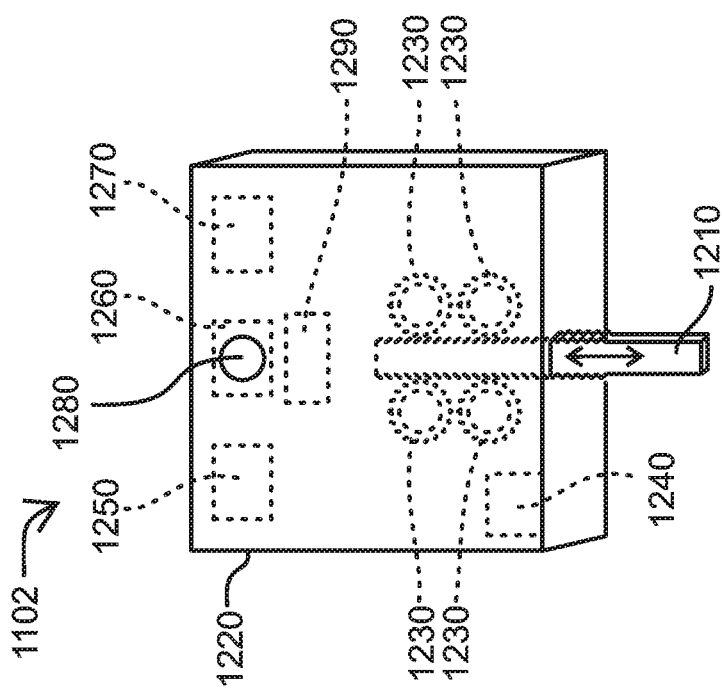

FIG. 17 illustrates the internal components of the control box 1220. CPU module 1250 is the central processing unit, and may be powered by battery module 1260. Wireless communication module 1270 allows for wireless communication with other components of the system, including, e.g., operator computerized device 104. In one embodiment, motor 1290 runs gears 1230 to position security rod 1210. Button 1280, which may be disposed on the outside of control box 1220, is used to access the battery module 1260. Button 1280 may alternatively be disposed anywhere that gives access to the battery module 1260.

In one arrangement, the key disabling device 1102 can include an ignition proximity sensor 1240 to detect when the key 109 is disposed inside or outside of the vehicle's ignition. In the case when the ignition proximity sensor 1240 detects the key 109 as being disposed outside of the vehicle's ignition, the control box 1220 can cause the security rod 1210 to be disposed in an extended position to block the key 109 from entering the ignition. In the case where the operator computerized device 104 transmits an open signal to the key disabling device communication port 1270, the control box 1220 retracts the rod 1210 relative to the device 1102 and the key 109 can fully be inserted into the ignition.

As an alternated to the proximity sensor 1240, the GPS mechanism of the operator computerized device 104 can communicate with the key disabling device 1102 to let it know when the driver is away from the vehicle 200 so that the security rod 1210 can be extended. As a further alternative to the proximity sensor 1240, a spring (not shown in the figures) may be attached to the end of the security rod 1210. When tension is detected in the spring, e.g., something is pressing on the spring, a signal may be sent to the control box 1220 to prevent the security rod 1210 from being extended. For example, the spring may be pressing against the ignition when the key 109 is in the ignition, and the security rod 1210 should not be extended while the key 109 is in the ignition. This is useful in the situation where the vehicle has been stopped for a set amount of time (e.g., 15 minutes) and the control box 1220 has been configured to extend the security rod 1210 after this set amount of time. If the key 109 is still in the ignition, the security rod 1210 should not be extended.

Figure 18:
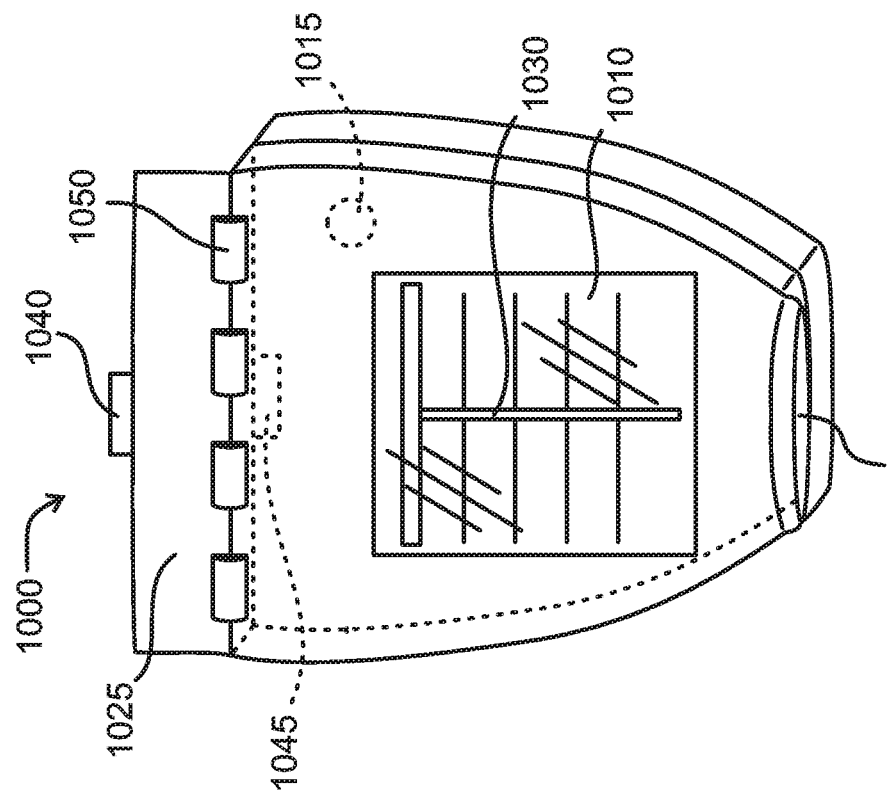
FIG. 18 illustrates a key disabling device of the vehicle driver monitoring system of FIG. 1, according to one arrangement.

FIG. 18 illustrates an alternate embodiment of a key disabling device, which may include one of more of the following: a locking door 1025, a key ring 1015, a stretchable rubber opening 1020, and a window 1010. In use, the supervisor slides the operator's key through the opening 1020 and locks the key into the adjustable and lockable overlapping key ring 1015. The key ring 1015 may use a clamp lock or may be electronically locked. After the locking door of 1025 of the key disabling device 1000 is closed by the supervisor and locked, the operator can access some key functions (unlock/lock, etc.) through the window 1010. The window 1010 can be open air or can be covered with a plastic, mesh, or other material.

The key disabling device 1000 may include hinges 1050 and a latch 1045 for use in closing and latching locking door 1025. A combination lock 1040 for locking the locking door 1025 may also be included. Alternatively, any other type of locking mechanism may be used to lock the locking door 1025. FIG. 18 further illustrates optional key ring track 1030 for adjusting the location of the key.

As indicated above, the configuration of the key disabling device 102 can depend upon the type of vehicle key used by the vehicle. For example, the key 109 can be configured as a wireless key that wirelessly interacts with the ignition of the vehicle, such as via radio frequency (RF). The following provides example embodiments of the key disabling devices 102 for wireless ignition keys 109.

FIGS. 19-22 illustrate an example embodiment of a wireless key disabling device 3102 configured to contain a wireless key 3109. FIG. 19 illustrates a front view of wireless key disabling device 3102. In one embodiment, the key disabling device 3102 includes a housing 3103 configured to hold the key 3109. The housing 3103 may include foam or rubber sides 3290 to help the fit of the shape of the key 3109 within the device 3102. Alternatively, no foam and/or rubber may be used. The housing 3103 may further include a window 3180 through which the buttons of the wireless key 3109 may be accessed. Window 3180 may be completely open or may be comprised of a clear plastic or mesh. Key ring lock 3110 may be used to hold wireless key 3109 in place.

FIG. 20 illustrates wireless key disabling device 3102 after it has been opened. Hinges 3120 allow device 3102 to be opened, enabling the insertion of wireless key 3109 into key holder 3210 on key side 3160. Key track 3170 may be used to enable wireless key 3109 to move, enabling access to buttons on wireless key 3109 through window 3180. The key track 3170 enables the wireless key 3109 to move to any location needed on key side 3160 to accommodate various sizes and placements of the key ring hole on the wireless key 3109. After the key has been inserted into key holder 3210, key side 3160 and window side 3150 may be swung together using hinges 3120 and latched or locked together using latch/lock parts 3130 and 3140. Latch/lock parts 3130 and 3140 may comprise a combination lock. Alternatively, any other type of locking mechanism may be used to lock the locking door. FIG. 21 illustrates wireless key disabling device 3102 in a side view after it has been closed. Note that hinges 3120 and latch/lock parts 3130 and 3140 are not illustrated in FIG. 17. FIG. 21 shows that the key disabling device 3102 is comprised of two sides, key holder 3210 (including both key side 3160 and window side 3150) and control box 3220.

Key disabling device 3102 may be configured to jam or prevent transmission of a wireless (e.g., RF) signal from the wireless key 3109 to the vehicle ignition when the operator places the wireless key 3109 in proximity to the vehicle ignition. This enables the wireless key 3109 to be used to enter the vehicle, and the signal jamming would start after the operator is inside the vehicle. Alternatively, the signal jamming may be configured to start after the doors of the vehicle are unlocked. In one embodiment, the housing 3103 is manufactured from an aluminum material or other signal jamming materials that limits or prevents transmission of the wireless signal from the wireless key 3109 to the vehicle ignition. In another arrangement, the key disabling device 3102 is configured with a wireless signal jamming mechanism. FIG. 22 illustrates control box 3220. Control box 3220 may include wireless signal jamming mechanism 3295 that can include one of more of a voltage controlled oscillator 3300, a tuning circuit 3310, an amplification unit 3320, and an antenna 3330. One of ordinary skill in the art would understand that these components may operate together to jam a wireless signal. During operation, the operator computerized device 104 is configured to provide an instruction signal to the key disabling device 3102 that either activates or deactivates the jamming mechanism 3295. Control box 3220 may also include CPU 3250, battery 3260 and wireless port 3270. Wireless port 3270 allows for wireless communication with other components of the system, including, e.g., operator computerized device 104.

In one embodiment, the operator computerized device 104 and/or the key disabling device 3102 can include a proximity sensor. In the case where the intoxication detection device 130 determines that the operator is in the vehicle, the proximity sensor generates and sends a notification signal to the operator computerized device 104. In response to receiving the notification signal, the operator computerized device 104 generates and transmits an initiation signal to the key disabling device 3102. The initiation signal notifies the key disabling device 3102 that the operator is in the vehicle 200 and that the key disabling device 3102 can activate the jamming mechanism 3295 to generate a jamming signal so that the operator can only start the vehicle after passing a sobriety test and providing identity information to the operator computerized device 104.

In one arrangement, the functionality of the wireless key disabling device 3102 is configured as part of a key chain 4000 as illustrated in FIG. 23. In this embodiment wireless key 3109 is not placed in a device. Key chain 4000 is attached to wireless key 3109 through the use of key ring lock 4110. Key chain 4000 may comprise CPU 4120, battery 4130, and wireless communication module 4150, which function as described above. Key chain 4000 may also comprise RF jamming components 4140, which may include a voltage controlled oscillator, a tuning circuit, and an amplification unit. These components function similarly to the RF jamming components described above with respect to FIG. 22.

As indicated above, the key disabling device 102 can be configured to prevent or allow either an operator's access to the functionality of a key 109, whether mechanical or electrical. In one arrangement, the key 109 includes a key blocking mechanism. Examples of the key blocking mechanism are provided below.

Figure 25:
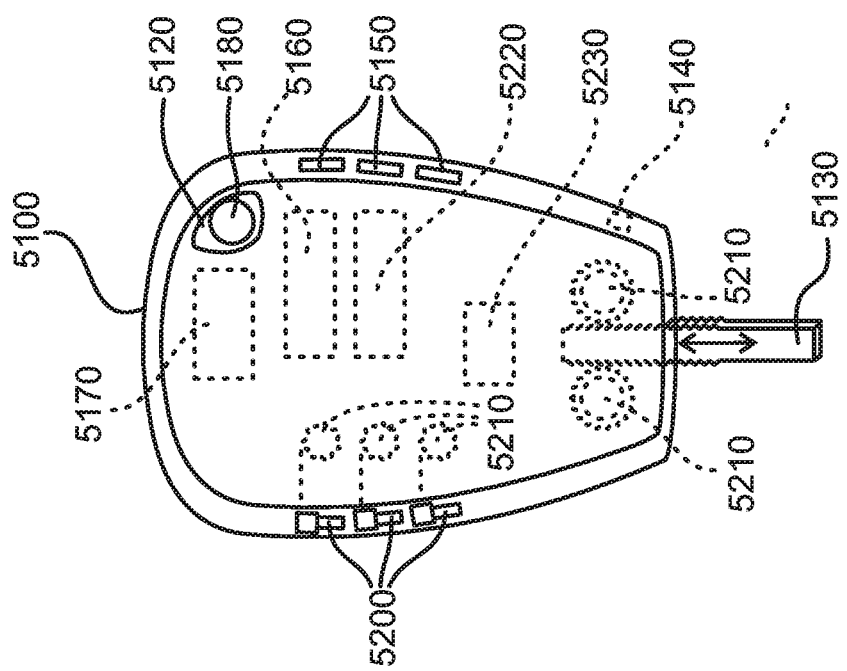
FIGS. 24 and 25 illustrate a key disabling device of the vehicle driver monitoring system of FIG. 1, according to one arrangement.
Figure 24:
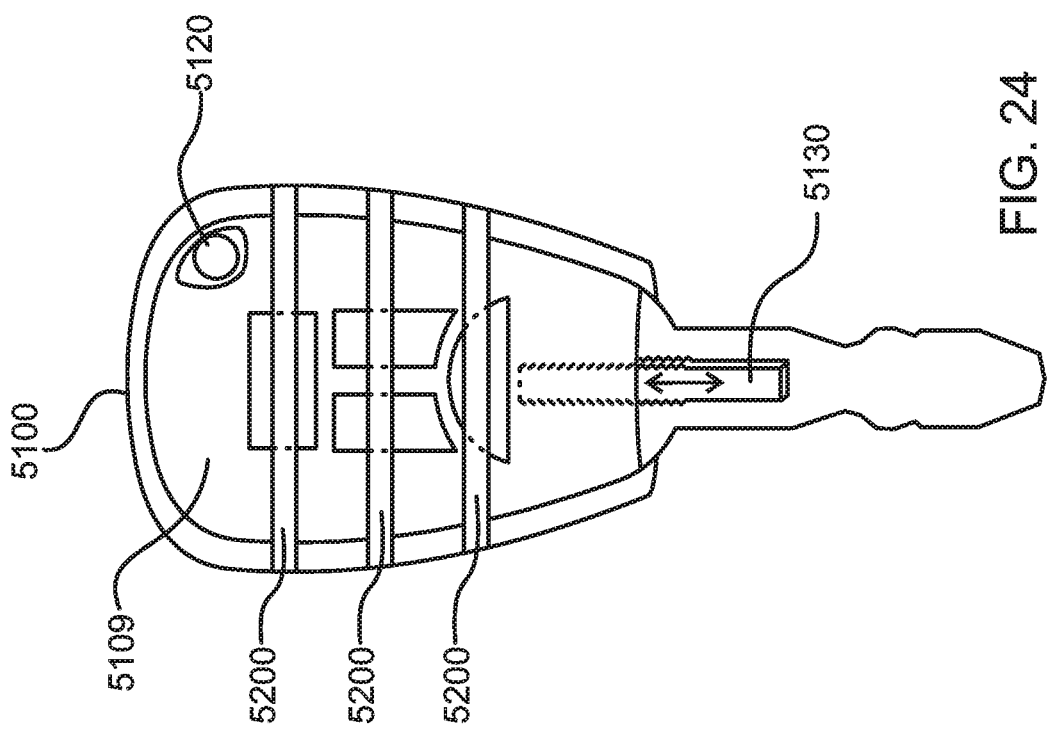

FIGS. 24 and 25 illustrate an arrangement of a key blocking mechanism 5100 where the key blocking mechanism 5100 attaches to the back of the key 5109 and is locked onto the key ring part 5120 of the key 5109 using a key ring lock gear 5180 that closes the overlapping key ring lock, such as via a spring. There can also be a key ring with a locking pin that attaches the key to the key blocking mechanism 5100. The supervisor of the operator can use the supervisor computerized device 106 to release and lock the key once they put it in the key blocking mechanism 5100. The key blocking mechanism 5100 has retractable straps 5200 attached to gears 5210 that attach to the strap receptacles 5150 on the other side of the key blocking mechanism 5100. The straps 5200 may alternatively be made out of a stretchable clear rubber that is not retractable or on gears, but just slides onto the key and then the key ring lock attaches to the key 5109. The straps 5200 may also be made out of a steel-coated wire, or any other suitable material. The key blocking mechanism 5100 may have an ignition proximity sensor 5140 to tell when the key is out of the ignition. Alternately, instead of using a proximity sensor, a GPS on the operator computerized device 104 can be used to communicate with the key blocking mechanism 5100 to let it know that the operator is away from the vehicle and the security rod 5130 should be extended. As a further alternative to the proximity sensor 5140, a spring (not shown in the figures) may be attached to the end of the security rod 5130.

The security rod 5130, in one arrangement, is configured as a toothed metal rod that is moved in and out of the key blocking mechanism 5100 by gears 5210 on either side of the rod 5130. The security rod 5130 may alternatively be configured as a non-toothed rod, as described above in more detail. When the key blocking mechanism 5100 is in locked mode, the rod 5130 extends so that the key 5109 will not be able to be put all the way in the ignition. When the operator computerized device 104 sends an open signal to the communication port 5220 of the key blocking mechanism 5100, the rod is retracted into the key blocking mechanism 5100 and the key 5109 can fully be inserted into the ignition. The key blocking mechanism 5100 may also comprise CPU 5170, battery 5160, and wireless communications module 5220, which function as described above. Motor 5230 may be used to move the gears 5210.

Figure 27:
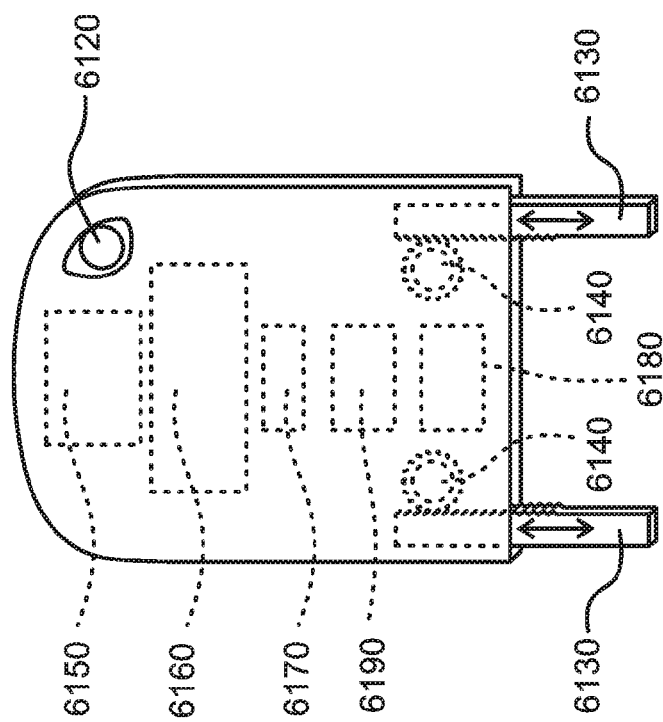
FIGS. 26 and 27 illustrate a key disabling device of the vehicle driver monitoring system of FIG. 1, according to one arrangement.
Figure 26:
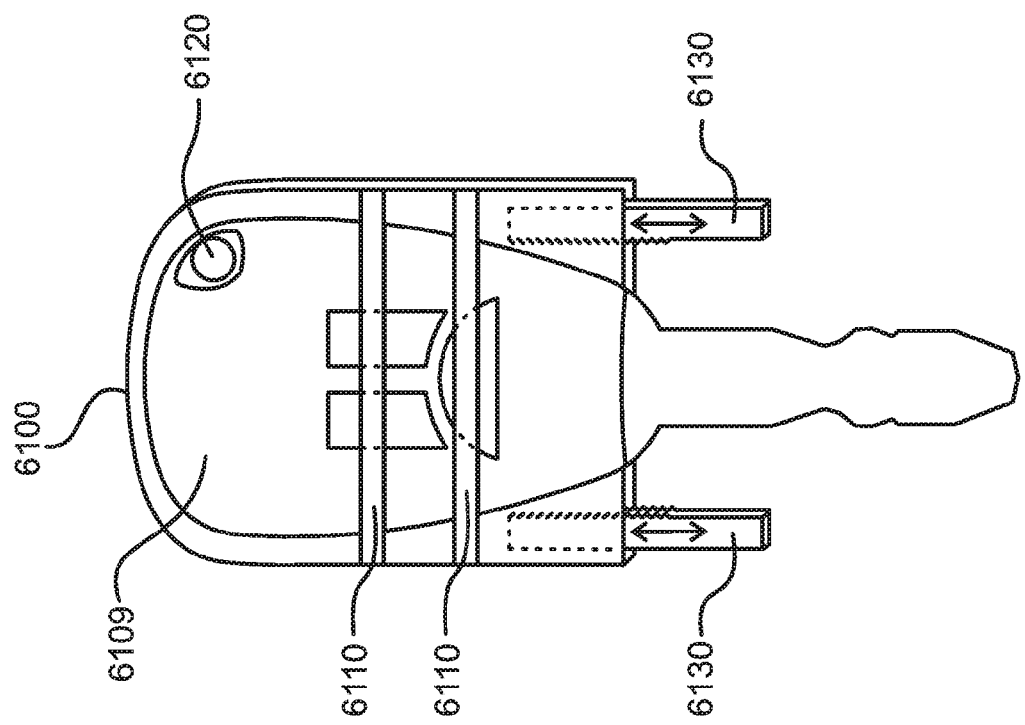

FIGS. 26 and 27 illustrate an alternative arrangement of a key blocking mechanism 6100. The key blocking mechanism 6100 attaches to the back of a key 6109 and includes two security rods 6130. The key blocking mechanism is otherwise similar to the key blocking mechanism 5100 described above in FIGS. 24 and 25. Key blocking mechanism 6100 may include straps 6110, key ring lock 6120, wireless communication module 6150, CPU 6160, battery 6170, ignition proximity sensor 6180, gears 6140, and motor 6190, all of which function substantially as described above with respect to FIGS. 24 and 25.

Figure 29:
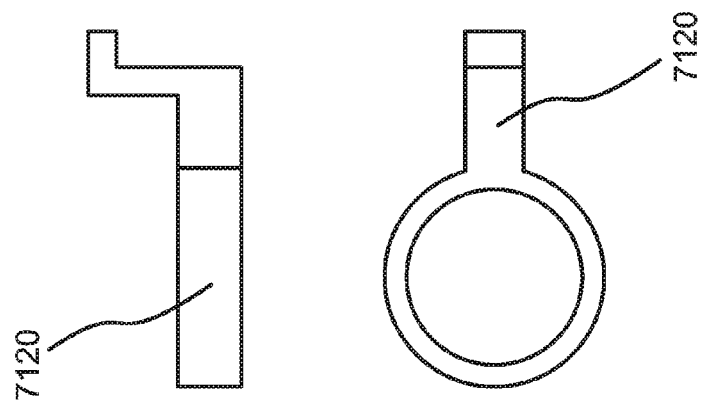
Figure 28:
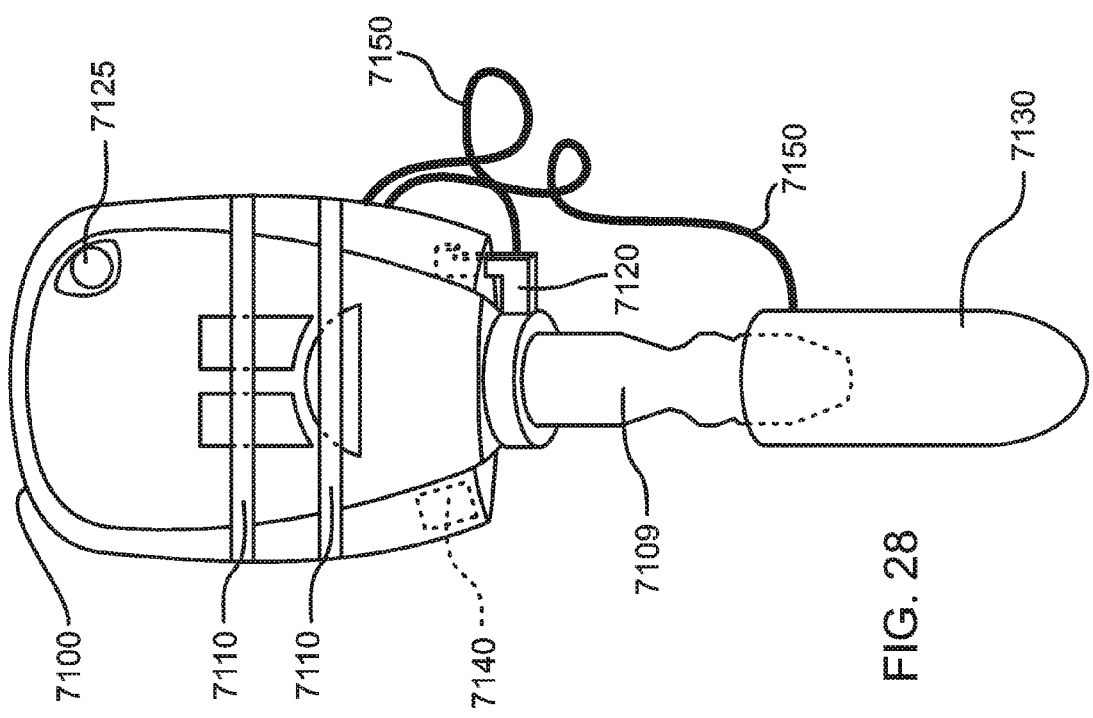

FIGS. 28-30 illustrate an arrangement of a key blocking mechanism 7100 that attaches to the back of the key 7109 and is locked onto key ring part 7125 of the vehicle key 7109 using the key ring lock gear that closes the overlapping key ring lock using a spring. There can also be a key ring with a locking pin that attaches the key to the key blocking mechanism 7100. The supervisor of the operator can use the operator computerized device 104 to release and lock the key once they put it in the key blocking mechanism 7100. The key blocking mechanism 7100 has straps 7110 that can be made out of a stretchable clear rubber that is not retractable or on gears, but just slides onto the key and then the key ring lock attaches to the key. The straps 7110 may also be made out of a steel-coated wire, or any other suitable material. The key blocking mechanism 7100 can also use retractable straps attached to gears that attach to the strap receptacles on the other side of the key blocking mechanism 7100, such as described above with respect to FIGS. 24-25. The key blocking mechanism 7100 has an ignition proximity sensor 7140 to tell when the key is out of the ignition. Alternately, instead of using a proximity sensor, a GPS or a spring may be used as described above.

The key blocking mechanism 7100 uses a key ring sheath 7130 or a key ring donut 7120 to secure the key 7109. The security key ring donut 7120 or sheath 7130 is on a retractable wire 7150 in the key blocking mechanism 7100. Unlike the other versions there is no automatic locking of the key; the operator has to lock the donut 7120 or the sheath 7130 onto the key themselves. FIG. 28 shows both donut 7120 and sheath 7130 on the key 7109; in operation only one of donut 7120 and sheath 7130 would be used. FIG. 29 shows side and top views of the key ring donut 7120. As illustrated, the key ring donut 7120 has a round opening which enables it to slide onto the key. FIG. 30 shows a side view of the key ring sheath 7130. The key ring sheath 7130 covers the key. Key blocking mechanism 7100 may also include a CPU, a battery, and a wireless communication module as described above for communication with an operator computerized device 104 and/or a supervisor computerized device 106. The key ring donut 7120 and/or sheath 7130 may be on a retractable wire 7150. Other means of securing the key ring donut 7120 and/or the sheath 7130 to the key blocking mechanism 7100 may be used.

Figure 31:
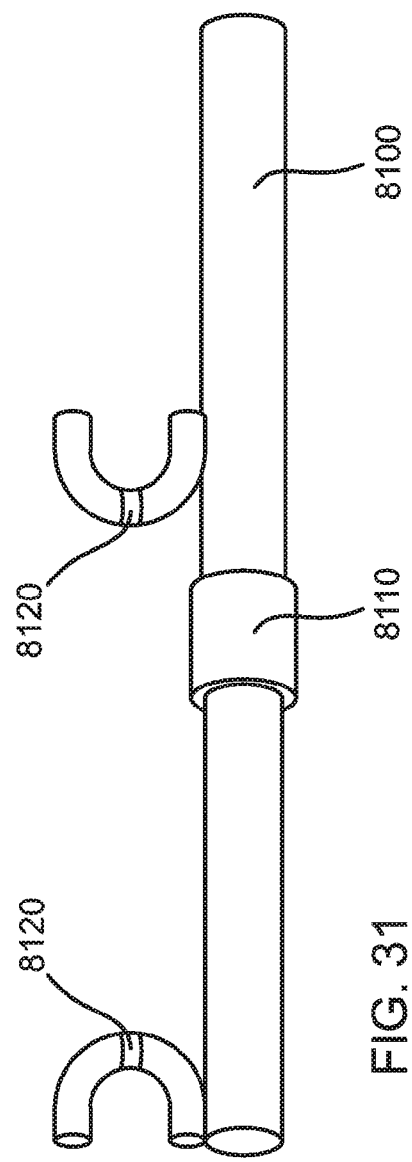
FIGS. 31-32 illustrate a wheel blocking mechanism according to one arrangement.
Figure 32:
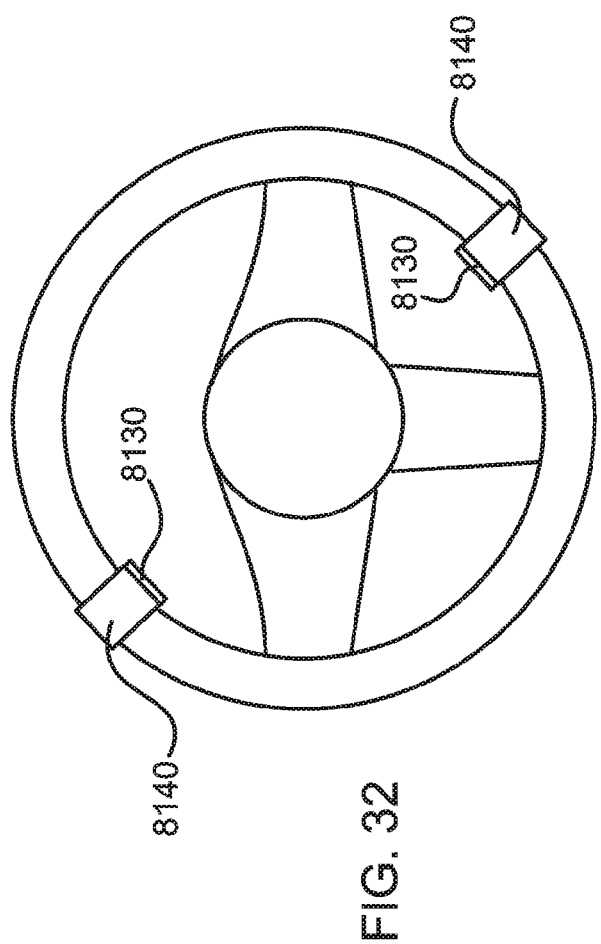

FIGS. 31 and 32 illustrate an embodiment of a steering wheel locking mechanism 8100 that may be used instead of a key blocking mechanism. The steering wheel locking mechanism is similar to the "club" steering wheel locking device, with a retractable rod that has curved portions that fit to the inside of the steering wheel. When the steering wheel locking mechanism is in place, it may be locked in place using lock 8110. Once the steering wheel locking mechanism 8100 is in place, it may send a signal, e.g., using Bluetooth or another wireless signaling technology, to operator computerized device 104, to let it know that the vehicle is inoperable. When the operator comes back to the vehicle, any required sobriety and/or identity recognition tests would need to be passed, as described above and in the accompanying Figures. After the required tests are passed, a signal would be sent to the steering wheel locking mechanism 8100 to unlock the lock 8110.

In one embodiment, steering wheel locking mechanism 8100 can detect that it is in place using sensors 8120. Steering wheel straps 8140 are previously attached to the steering wheel, and may contain sense elements 8130, which can be detected by sensors 8120 when sensors 8120 are in proximity to sense elements 8130. As an example, sense elements 8130 may comprise metal bolts that are detected by sensors 8120. When sensors 8120 detect sense elements 8130, the signal described above may be sent to the operator computerized device and/or the supervisor computerized device. Additionally, lock 8110 may automatically lock when sensors 8120 detect sense elements 8130. Straps 8140 may be made of any suitable material, e.g., fabric, rubber, metal, rubber coated steel wire, etc.

In an alternative embodiment, steering wheel locking mechanism 8100 can detect that it is in place using a sensor located near the steering wheel instead of on the steering wheel. As a further alternative, the operator may take a photo of the steering wheel locking mechanism 8100 locked in place, and the operator computerized device and/or the supervisor computerized device would receive the photo and detect that the steering wheel locking mechanism 8100 is locked in place.

The key disabling device 102, operator computerized device 104, and supervisor computerized device 106 may be implemented in any number of computing devices. Typically, instructions are laid out on computer readable media, generally non-transitory, and these instructions are sufficient to allow a processor in the computing device to implement the method of the invention. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file—storing medium. The outputs may be delivered to a user by way of a video graphics card or integrated graphics chipset coupled to a display that maybe seen by a user. Alternatively, a printer may be employed to output hard copies of the results. Given this teaching, any number of other tangible outputs will also be understood to be contemplated by the invention. For example, outputs may be stored on a memory chip, hard drive, flash drives, flash memory, optical media, magnetic media, or any other type of output. It should also be noted that the invention may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi—connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method.

While various embodiments of the innovation have been particularly shown and described, it will be understood by those skilled in the art that various changes in form and details may be made therein without departing from the spirit and scope of the innovation as defined by the appended claims.

For example, as illustrated in FIG. 1, the key disabling device 102, the operator computerized device 104, and the intoxicant detection device 130 are configured as discrete, separate devices. Such illustration is by way of example only. The devices can be integrated in a number of ways. For example, the functionality of the key disabling device 102 and the intoxicant detection device 130 can be integrated in a single unit. In another example, the functionality of the key disabling device 102, the operator computerized device 104, and the intoxicant detection device 130 are integrated into a single unit.

As described above, supervisors can activate the key disabling device 102. This description is by way of example only. In one arrangement, in the case where the child operator does not live with the parent, e.g., if they are at college, the vehicle key can remain attached to the key disabling device and the application 142 of the operator computerized device can be configured to be activated only during certain times. In such an arrangement, the application 142 is either continuously active or becomes active in response to the key disabling device 102 becoming active.

In addition, while various key blocking methods and mechanisms have been described, any system or method for preventing operation of the vehicle may be used, including, but not limited to, a steering wheel lock (ie. "the club"), a bar lock, a tire lock or boot, a brake pedal and/or gas pedal lock, an ignition lock, a shift lock, a gear stick lock, a gear shift lock, a gear selector lock, an engine disabler, an engine kill switch, a fuel switch, a time delay switch, a time delay ignition, a clutch lock, a clutch and brake lock, a brake lock on hydraulic system, an alternator disabler, a windshield viewing locking shield, an ignition interlock, and a battery cutoff lock.

In one arrangement, the system 100 can be used for the parental market and for the supervised transportation, government jobs, insurance reduction, and DUI markets.

Certain features described in the context of various embodiments are not to be considered essential features of those embodiments, unless the embodiment is inoperative without those elements.

A detailed description of one or more embodiments of the invention is provided herein along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the description herein in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

For the sake of clarity, processes and methods herein may have been illustrated with a specific flow, but it should be understood that other sequences may be possible and that some may be performed in parallel, without departing from the spirit of the invention. Additionally, steps may be subdivided or combined. It will be understood by one of ordinary skill that an embodiment can contain an alternate order of the steps, or an alternate configuration or arrangement of elements, adapted to a particular application disclosed herein. All such variations and modifications are intended to fall within the scope of this disclosure. The depiction and description of steps in any particular order or elements in any particular arrangement is not intended to exclude embodiments having the steps in a different order or elements in a different arrangement, unless required by a particular application, explicitly stated, otherwise clear from the context, or unless the order or arrangement would render an embodiment inoperative. Although the present invention has been described above in terms of specific embodiments, it is anticipated that alterations and modifications to this invention will no doubt become apparent to those skilled in the art and may be practiced within the scope and equivalents of any appended claims.

What is claimed is:

1. A vehicle driver monitoring system, comprising:
   a proximity sensor;
   an operator computerized device comprising a processor; and a memory storing instructions that, when executed by the processor, cause the operator computerized device to perform the operation of:
   receiving a signal from the proximity sensor indicating that the operator is within a pre-defined proximity of the vehicle;
   providing an alert to an operator indicating the operator is permitted to operate a vehicle in response to receiving and testing operator identification information and information regarding the level of an ingestible substance; and
   a supervisor computerized device comprising a processor; and a memory storing instructions that, when executed by the processor, cause the supervisor computerized device to perform the operation of:
   receiving and saving vehicle monitoring information sent by the operator computerized device.

2. The vehicle driver monitoring system of claim 1, further comprising:
   a key disabling device;

wherein the key disabling device is configured to selectively prevent use of a vehicle key at least partly contained therein, wherein a functional part of the key is accessible to the operator while use of the key is prevented;

wherein the key disabling device is further configured to allow use of the vehicle key in response to receiving a signal from the operator computerized device, wherein the signal is based on the operator identification information and information regarding the level of an ingestible substance.

3. The system of claim 2, wherein the key comprises a wireless key.

4. The system of claim 1, wherein the ingestible substance is alcohol.

5. The system of claim 1, wherein the operator computerized device is configured to alert a supervisor when the level of the ingestible substance is outside of the pre-defined limits.

6. The system of claim 5, wherein the operator computerized device is configured to display to the operator information about a ride service when the level of the ingestible substance is outside the pre-defined limits.

7. The system of claim 1, wherein the operator computerized device is further configured to:

compare time stamps of the substance test and the identification information test; and alert a supervisor and signal the operator to not drive when the time stamps are not reasonably contemporaneous.

8. The system of claim 1, wherein the operator identification information comprises an image of the operator's face.

9. The system of claim 1, wherein the operator computerized device is further configured to:

receive a vehicle operation restriction, wherein the vehicle operation restriction comprises one or more of the following: a time period and a geographic area; and notify the supervisor when the vehicle operation restriction is violated.

10. The system of claim 1, wherein the supervisor computerized device is further configured to:

provide the vehicle monitoring information for use in calculating an insurance discount based on the provided information.

11. A method for monitoring the operation of a vehicle by an operator of the vehicle, the method comprising:

receiving, by an operator computerized device, a signal indicating that the operator is within a pre-defined proximity of the vehicle;

receiving, by the operator computerized device, a signal indicating a level of an ingestible substance with respect to the operator;

sensing, by the operator computerized device, identification information of the operator;

comparing, by the operator computerized device, the identification information with a database of stored identification information to confirm the identity of the operator; and providing, by the operator computerized device, an alert to the operator that the operator is permitted to operate the vehicle upon confirmation of the identity of the operator and further upon the level of the ingestible substance being with pre-defined limits.

12. The method of claim 11, further comprising the steps of:

preventing use of the vehicle by the operator; and allowing the operator to use the vehicle upon confirmation of the identity of the operator and further upon the level of the ingestible substance being with pre-defined limits.

13. The method of claim 12, wherein use of the vehicle is enabled by a key, and further wherein the key comprises a wireless key.

14. The method of claim 11, wherein the ingestible substance is alcohol.

15. The method of claim 11, further comprising the step of:

alerting a supervisor when the level of the ingestible substance is outside of the pre-defined limits or the identity of the operator cannot be confirmed.

16. The method of claim 15, further comprising the step of:

recording a video of the operator while the operator is performing the ingestible substance test for review by the supervisor.

17. The method of claim 11, further comprising the step of:

displaying on the operator computerized device information about a ride service when the level of the ingestible substance is outside the pre-defined limits.

18. The method of claim 11, wherein the identification information comprises an image of the operator's face.

19. The method of claim 11, wherein the identification information comprises information regarding the retina of the operator.

20. The method of claim 11, further comprising the steps of:

comparing time stamps of the substance test and the identification information test; and alerting a supervisor and signaling the operator to not drive when the time stamps are not reasonably contemporaneous.

21. The method of claim 11, further comprising the steps of:

monitoring operating conditions of the vehicle as the vehicle is being operated by the operator; and providing the monitored operating conditions for use in calculating an insurance discount based on the monitored operating conditions.

22. The method of claim 11, further comprising the steps of:

receiving a vehicle operation restriction, wherein the vehicle operation restriction comprises one or more of the following: a time period and a geographic area; and notifying the supervisor when the vehicle operation restriction is violated.

* * * * *